(12) United States Patent
Klecker et al.

(10) Patent No.: US 8,662,470 B2
(45) Date of Patent: Mar. 4, 2014

(54) DENTAL SYRINGE

(75) Inventors: Glenn A. Klecker, Silverton, OR (US);
David Terrill, Newberg, OR (US); Jason Spencer, Tega Cay, SC (US)

(73) Assignee: Dental Components LLC, Newberg, OR (US)

( * ) Notice: Subject to any disclaimer, the term of this patent is extended or adjusted under 35 U.S.C. 154(b) by 204 days.

(21) Appl. No.: 12/764,484

(22) Filed: Apr. 21, 2010

(65) Prior Publication Data

US 2010/0263733 A1    Oct. 21, 2010

Related U.S. Application Data

(60) Provisional application No. 61/171,272, filed on Apr. 21, 2009, provisional application No. 61/288,691, filed on Dec. 21, 2009.

(51) Int. Cl.
*F16K 47/00* (2006.01)

(52) U.S. Cl.
USPC .......................... 251/122; 251/322; 137/625.3

(58) Field of Classification Search
USPC ......... 251/120, 121, 122, 319, 320, 321, 322, 251/339; 137/625.3
See application file for complete search history.

(56) References Cited

U.S. PATENT DOCUMENTS

| | | | |
|---|---|---|---|
| 2,713,989 A | | 7/1955 | Bryant |
| 3,552,442 A | | 1/1971 | Knowles |
| 4,149,315 A | * | 4/1979 | Page et al. ...................... 433/114 |
| 4,572,238 A | * | 2/1986 | Stenlund ..................... 137/625.3 |
| 4,901,978 A | * | 2/1990 | Feild .............................. 251/282 |
| 5,045,055 A | * | 9/1991 | Gonser et al. ................... 604/33 |
| 5,848,893 A | | 12/1998 | Martin et al. |
| 6,076,552 A | * | 6/2000 | Takahashi et al. ......... 137/625.3 |
| 6,247,929 B1 | | 6/2001 | Bachman et al. |
| 6,349,920 B1 | * | 2/2002 | Lewis et al. .................... 251/122 |
| 7,114,699 B2 | * | 10/2006 | Hull et al. ...................... 251/121 |
| 2005/0016597 A1 | * | 1/2005 | Hope et al. ............... 137/516.27 |

FOREIGN PATENT DOCUMENTS

| | | |
|---|---|---|
| DE | 83 29 505 U1 | 4/1986 |
| WO | WO-2009/077923 A1 | 6/2009 |

OTHER PUBLICATIONS

"Dental Equipment Parts: Dental Service Parts—Parts Warehouse: Syringes," printed Jul. 30, 2010, < http://www.dentalequipmentsparts.com/dental-service-parts/parts-warehouse/parts-warehouse-contour-syringe-spool-valve.html>.
International Search Report and Written Opinion for corresponding International Appl. No. PCT/US2010/031895, mailed Jun. 28, 2010.
Martin, M.V., "The Air/Water Syringe: a Potential Source of Microbial Contamination," *British Dental Journal*, vol. 184, No. 6, Mar. 28, 1998, pp. 278-279.

\* cited by examiner

*Primary Examiner* — John K Fristoe, Jr.
*Assistant Examiner* — Reinaldo Sanchez-Medina
(74) *Attorney, Agent, or Firm* — Alston & Bird LLP

(57) ABSTRACT

A dental syringe may include a replaceable valve cartridge containing one or more valves which may use a seating surface and an opposing seating surface with a relative angle formed between the two surfaces. The relative angle allows for regulation of the flow of fluid. The replaceable valve cartridge may also include a system to remove a residual liquid from a tip of a dental syringe. Additionally, the replaceable valve cartridge may include a seal that prevents bleed-over of fluids. Further, the dental syringe may comprise a tip retention insert which may use either a pair of plates or a plurality of ball bearings to retain the dental syringe tips. An alternate embodiment of a valve may comprise features intended to reduce the force necessary to actuate the valve. A metering screw and/or flow-control groove with increasing depth may control of flow through the valve.

23 Claims, 33 Drawing Sheets

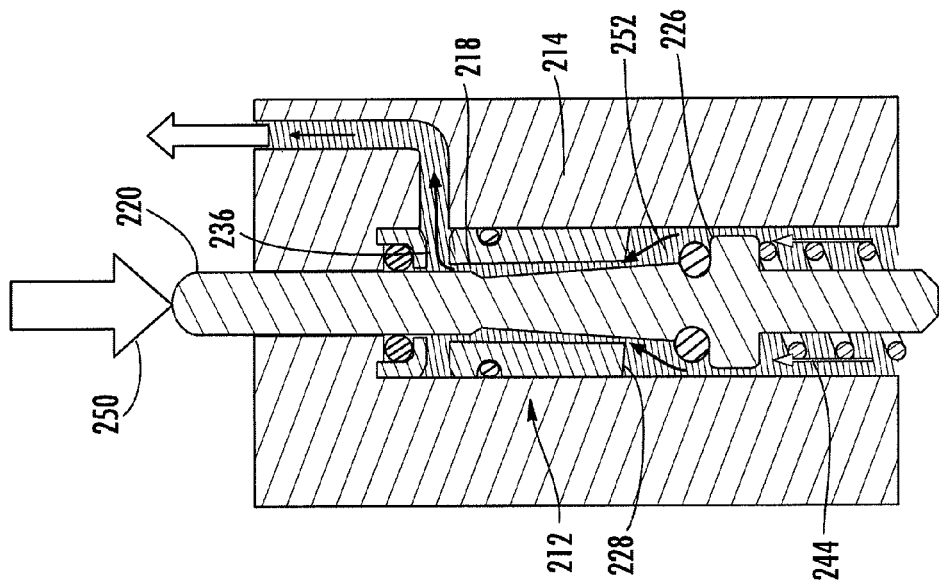
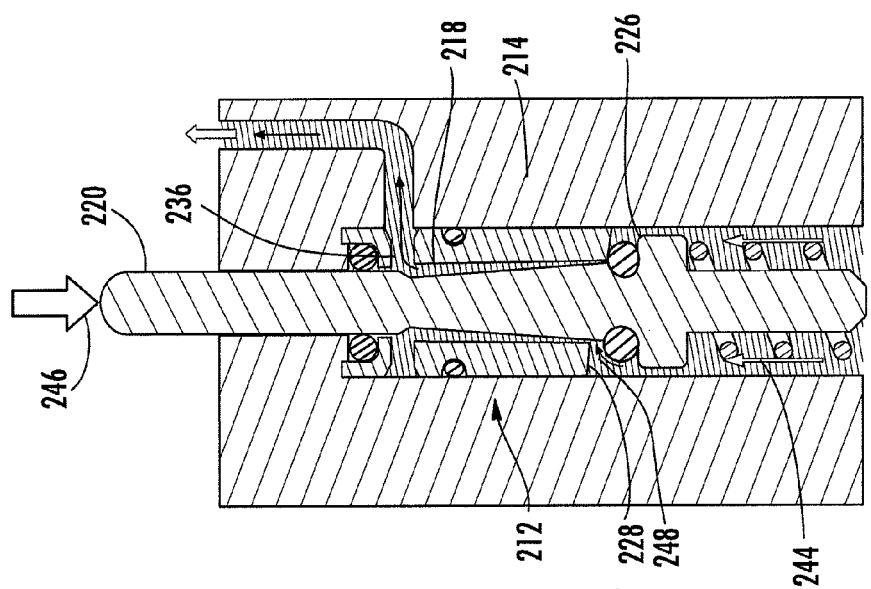
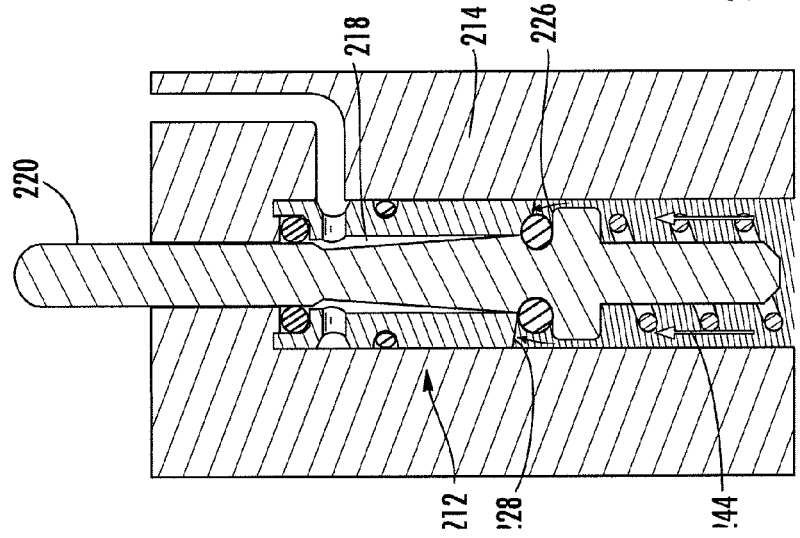

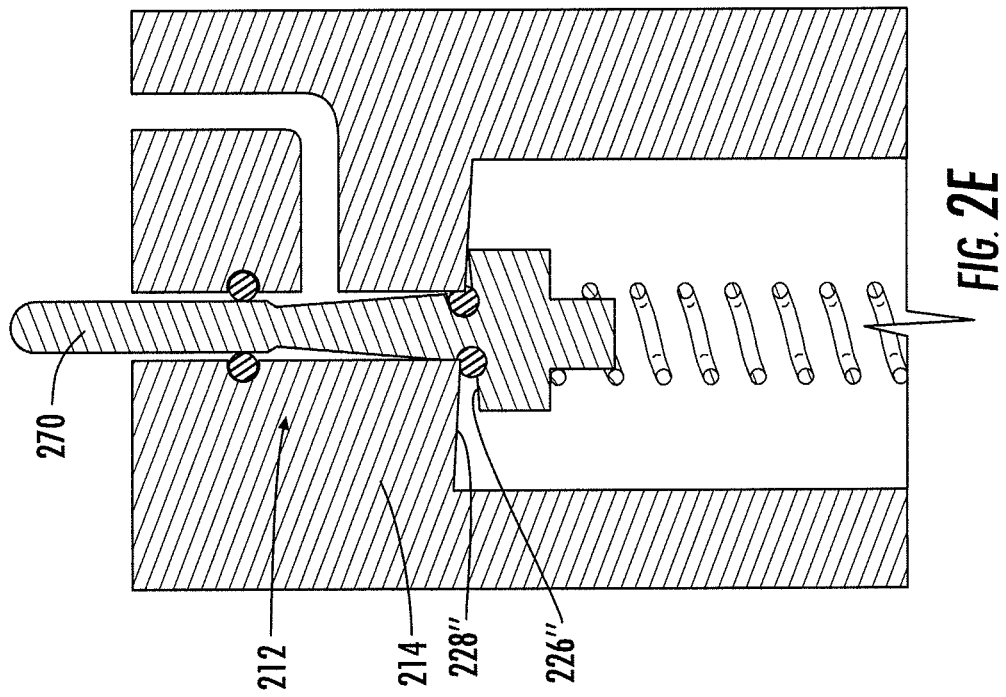
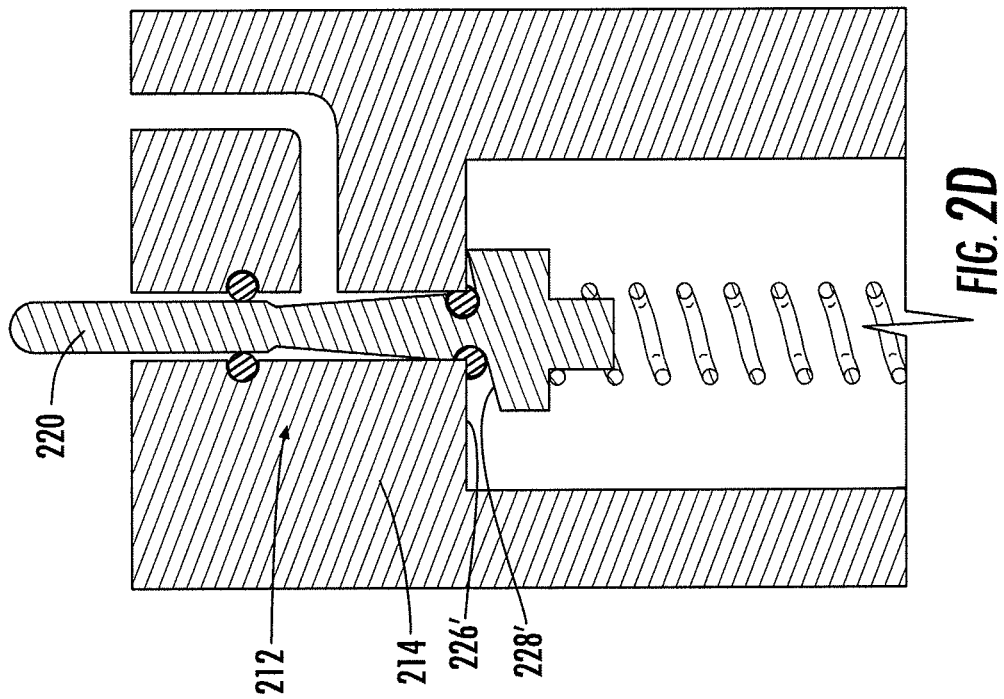

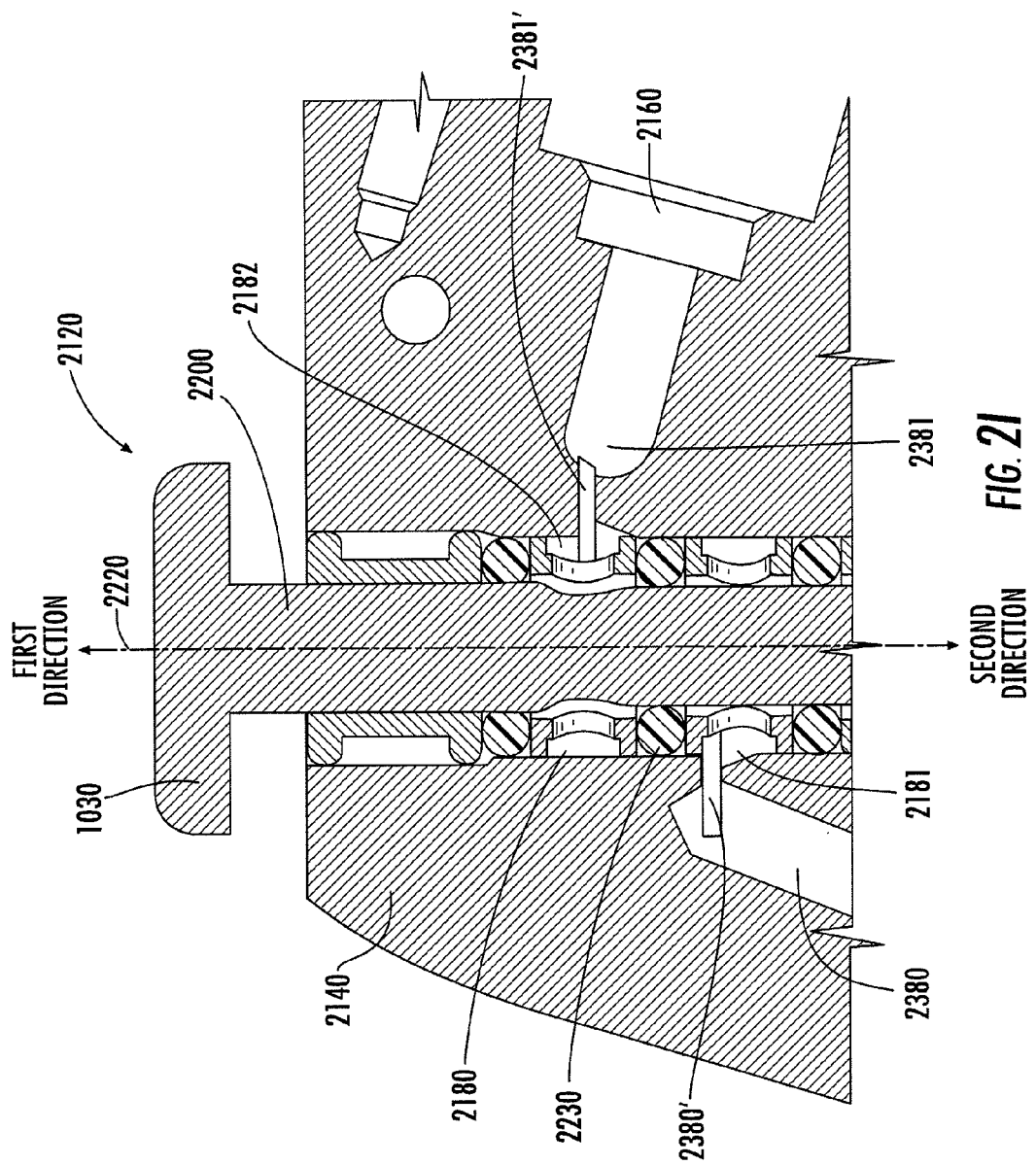

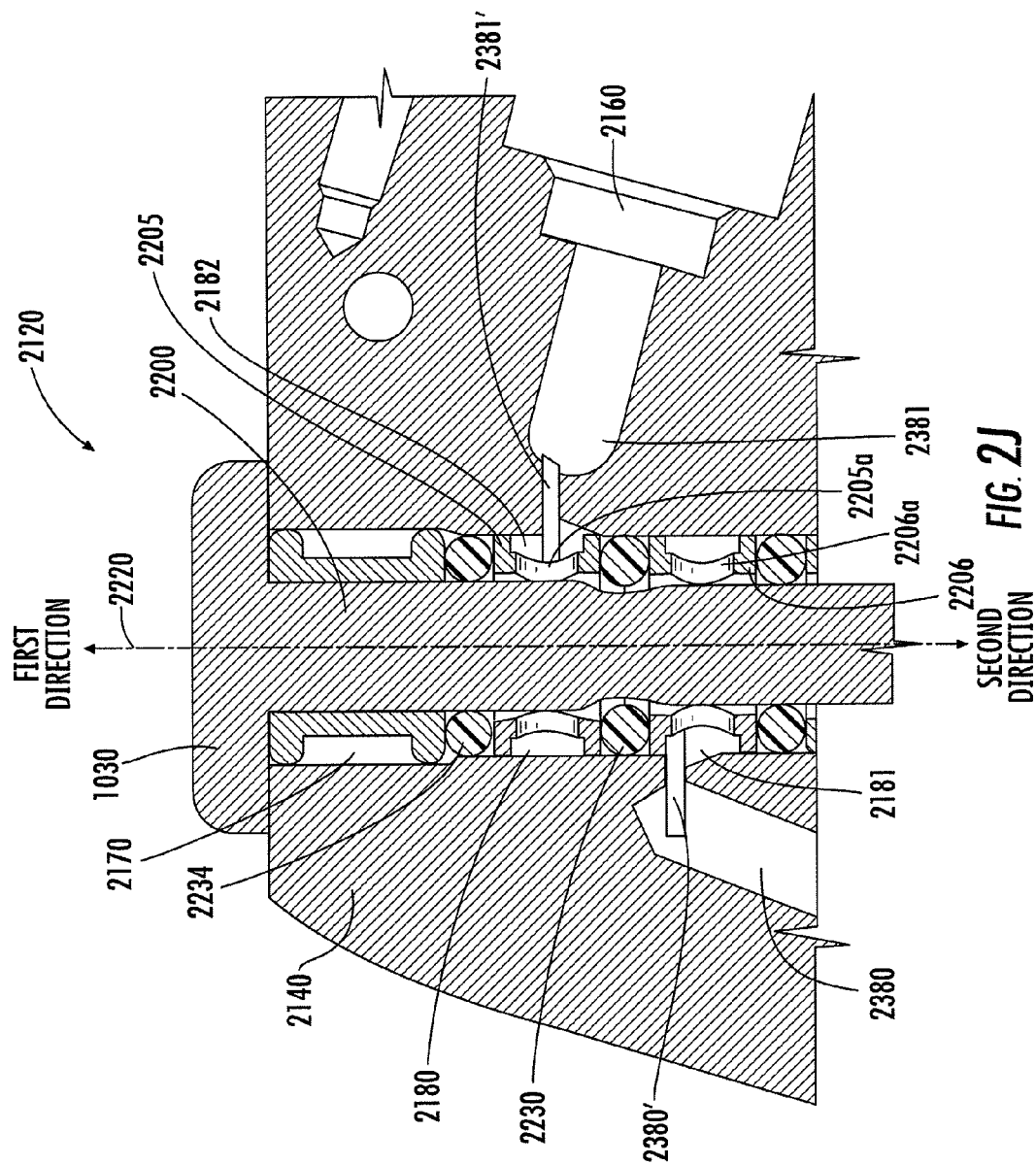

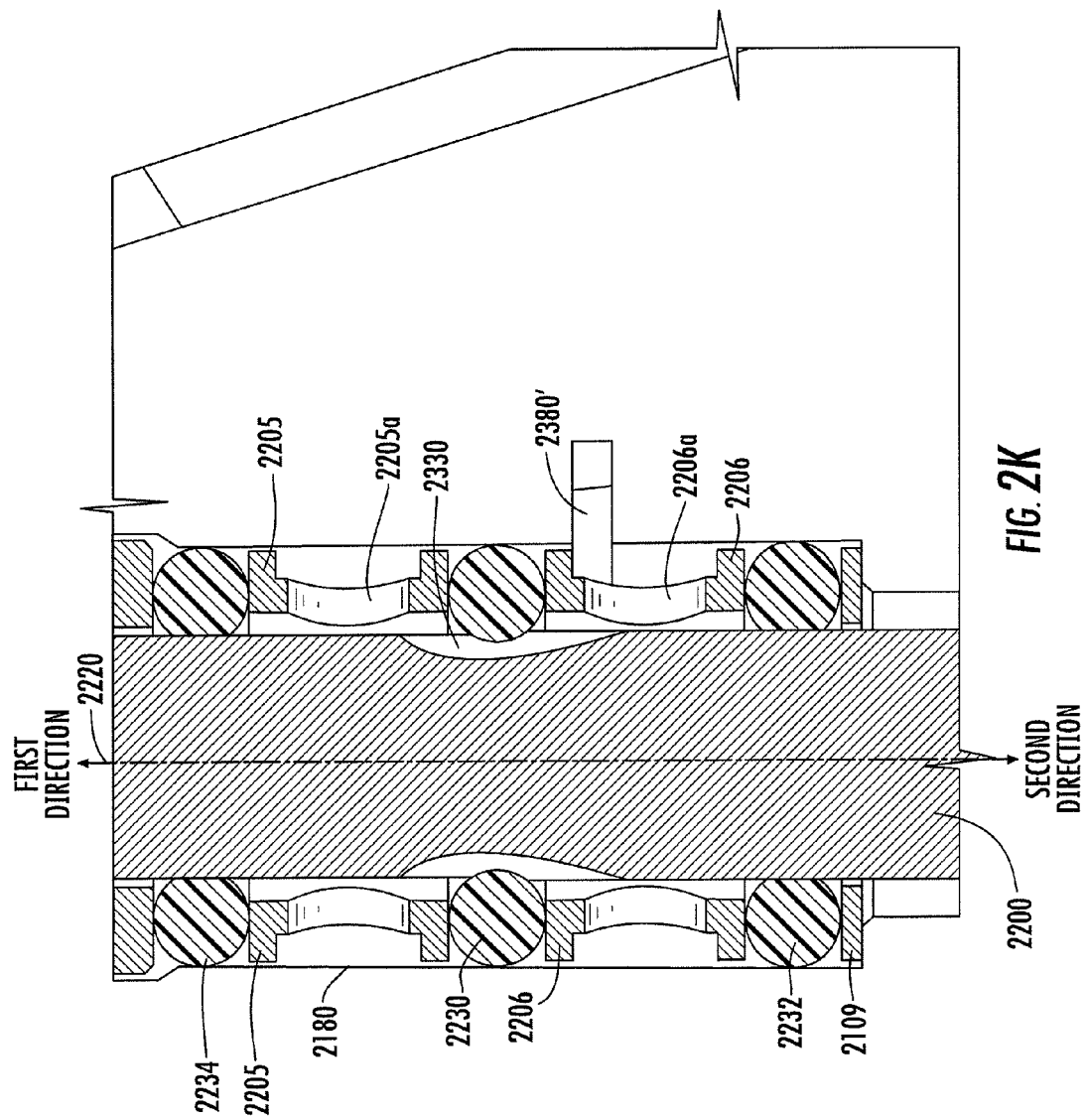

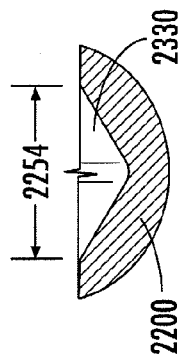
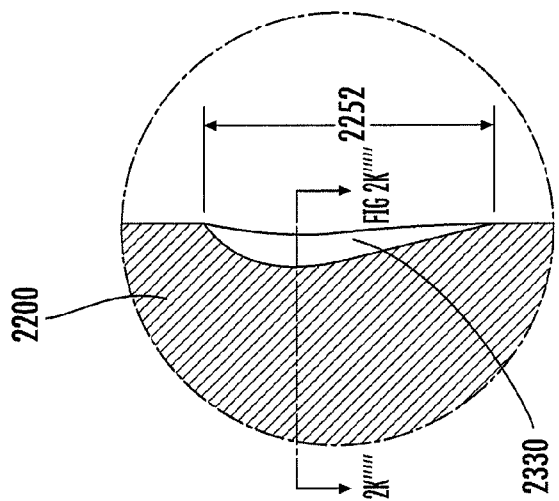
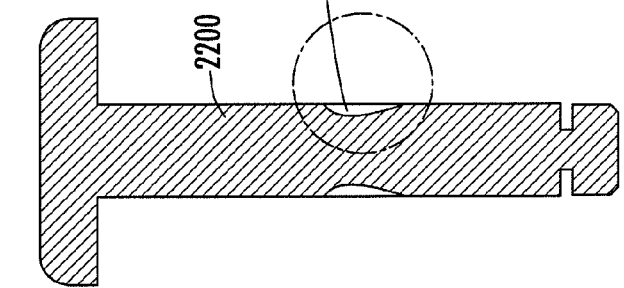
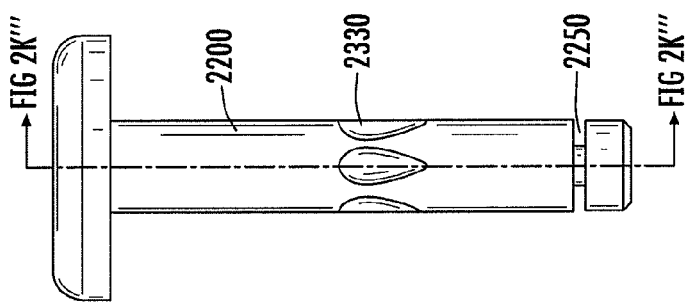

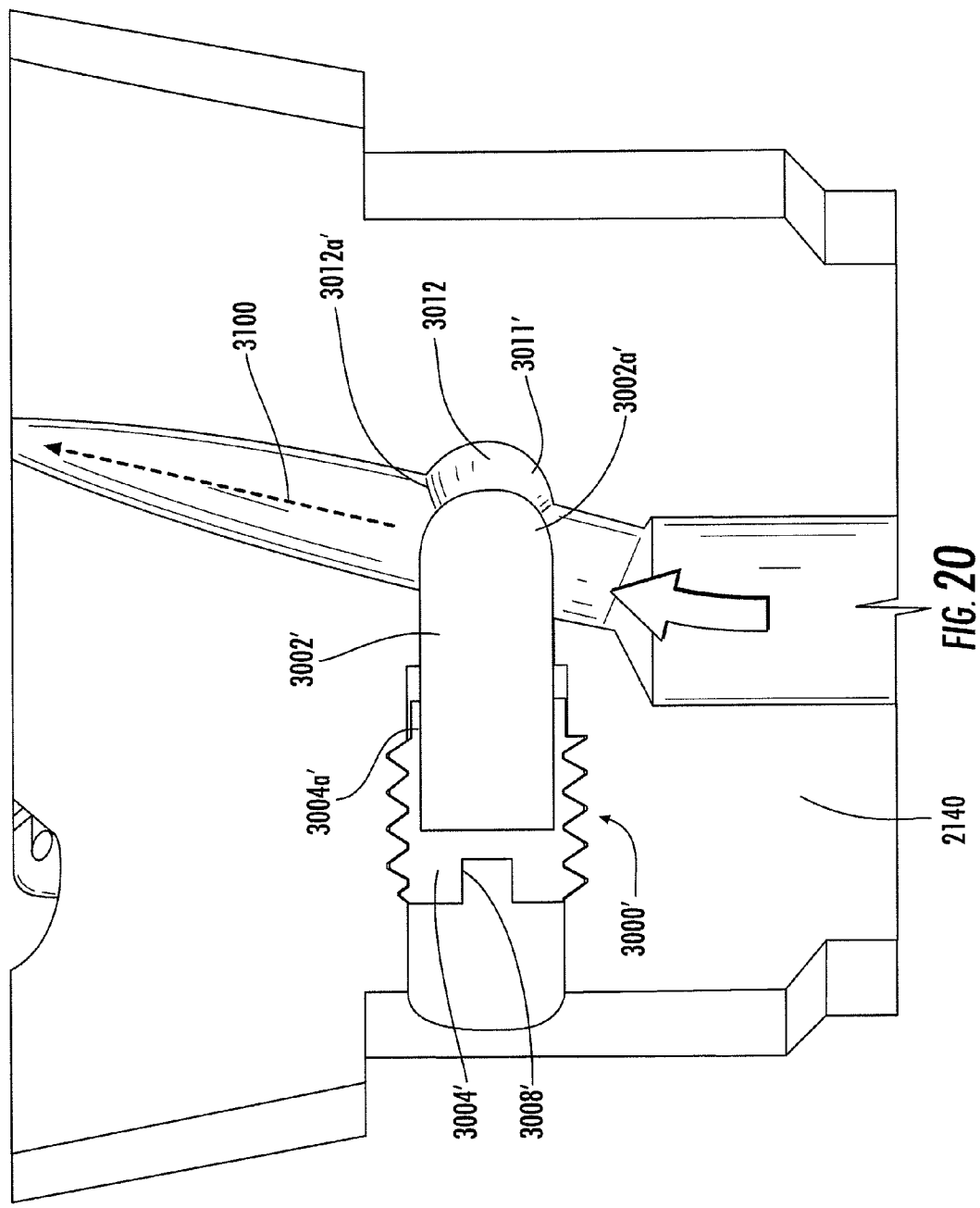

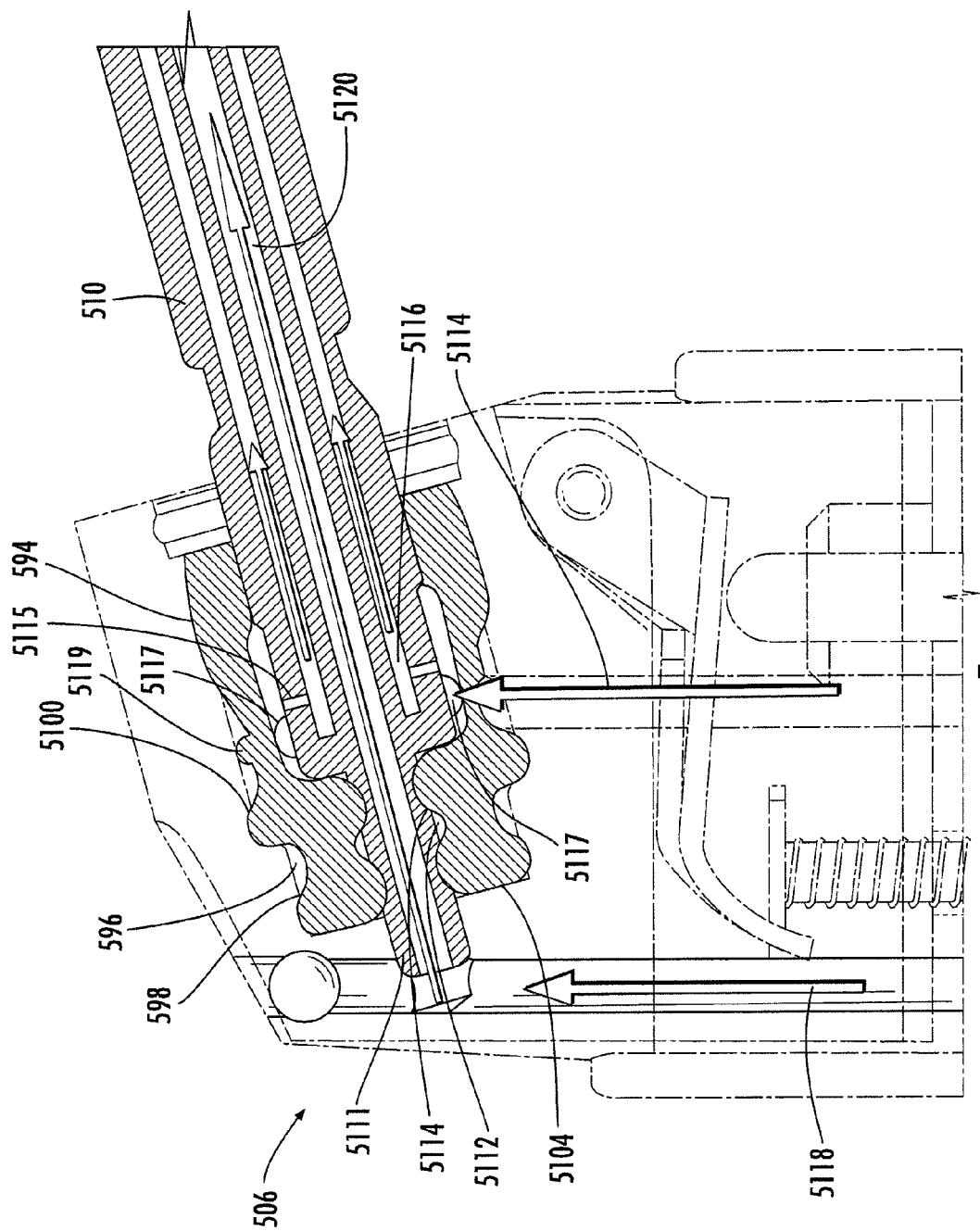

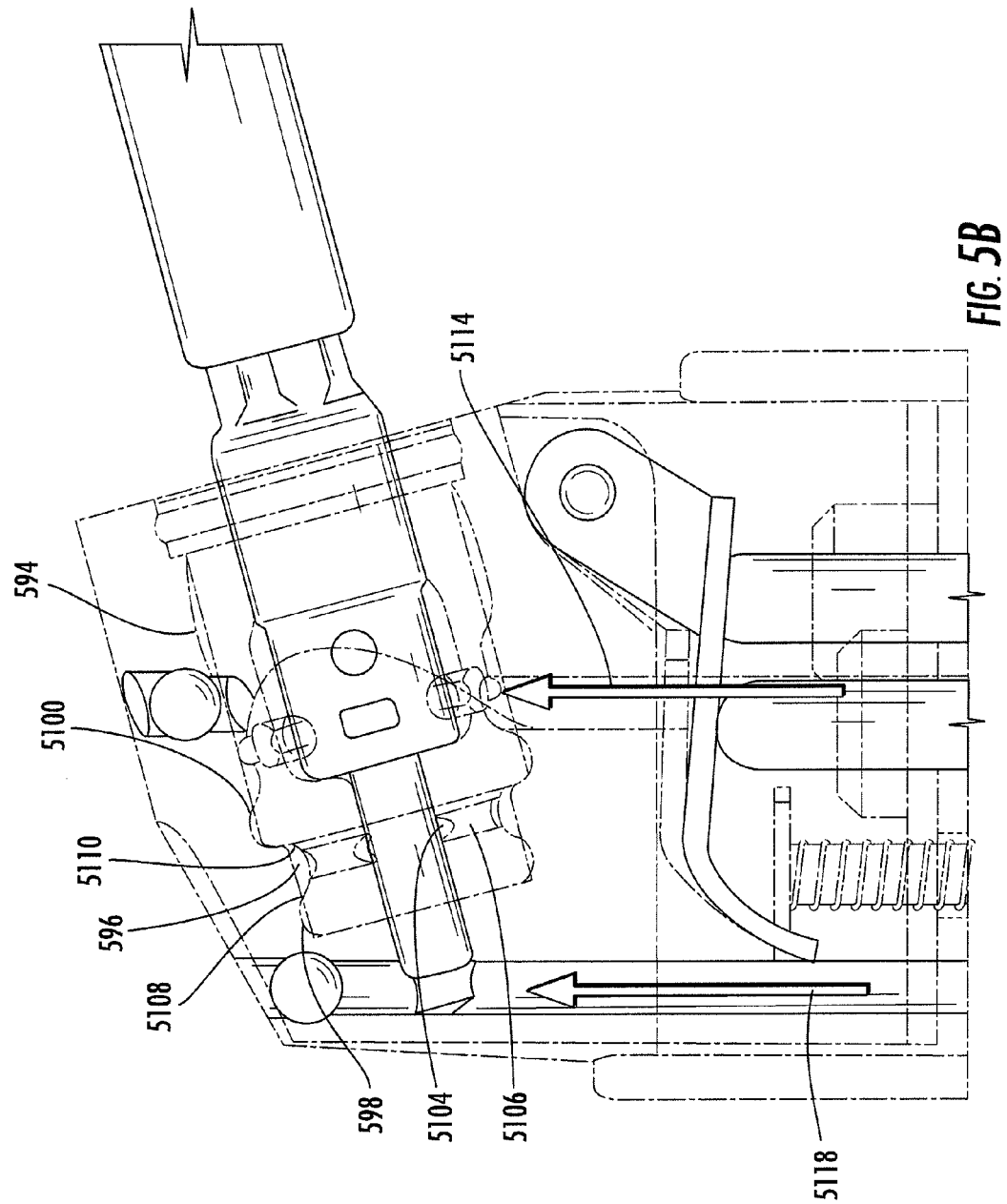

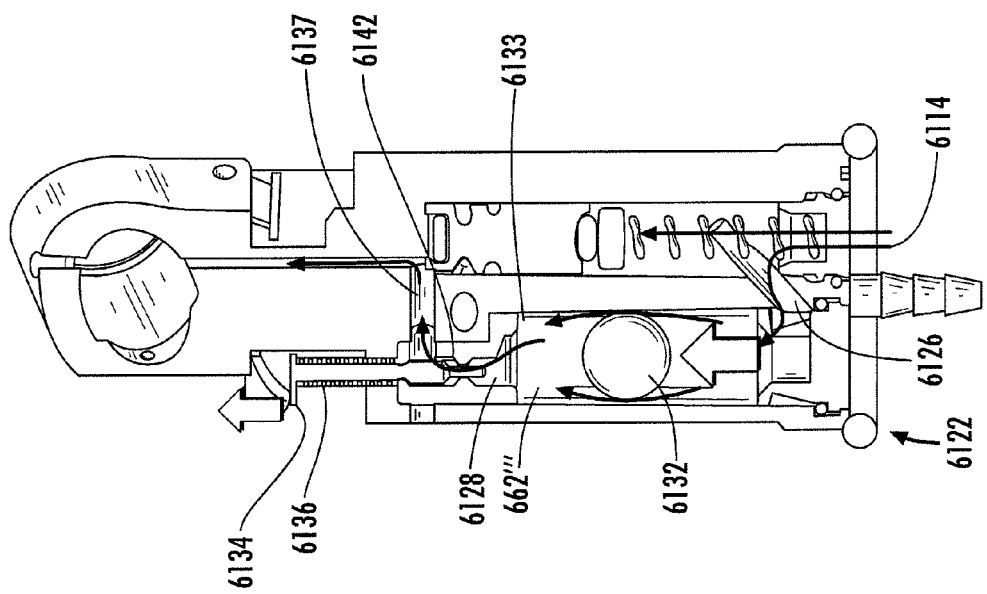
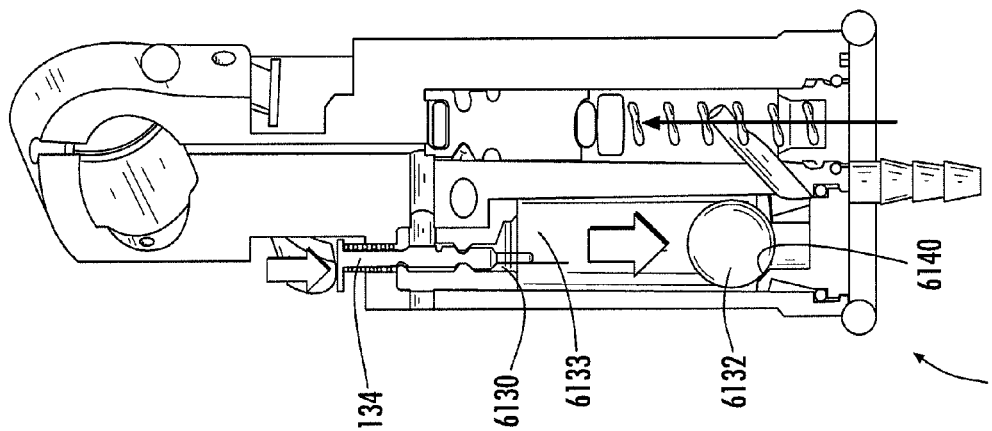
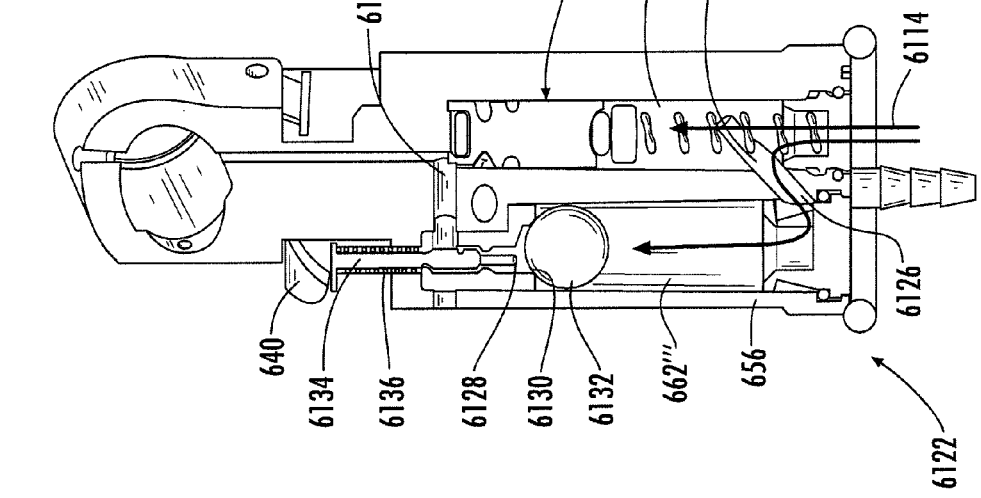

DENTAL SYRINGE

CROSS REFERENCE TO RELATED APPLICATIONS

This application claims priority from U.S. Provisional Application No. 61/171,272, filed Apr. 21, 2009 and U.S. Provisional Application No. 61/288,691, filed Dec. 21, 2009, both of which are hereby incorporated herein in their entirety by reference.

BACKGROUND

1. Field of the Invention

Embodiments of the invention relate to dental syringes and corresponding apparatuses and methods.

2. Description of Related Art

Dental syringes are known tools within the medical and dental industries that are typically used to supply air, water, heated water, medicine, or a combination thereof to the oral cavity. A dental syringe can also be used to evacuate the oral cavity by providing a vacuum function. Dental syringes can be used to clean and remove unwanted substances from targeted areas of the oral cavity such as saliva, blood, or debris resulting from procedures carried out on portions of the oral cavity. A dental syringe tip having one or more channels defined therein connects with the dental syringe and provides a way to direct the fluids from the dental syringe to specific areas of the oral cavity. The syringe tip may be replaceable from the body of the syringe after the syringe tip becomes contaminated or damaged, or as a precautionary measure. Supplies of pressurized water and air connect to the syringe to provide the fluids necessary for operation of the dental syringe.

BRIEF SUMMARY

A dental syringe may include a replaceable valve cartridge containing one or more valves which may use a seating surface and an opposing seating surface with a relative angle formed between the two surfaces. The relative angle allows for regulation of the flow of fluid. The replaceable valve cartridge may also include a system to remove a residual liquid from a tip of a dental syringe. Additionally, the replaceable valve cartridge may include a seal that prevents bleed-over of fluids. Further, the dental syringe may comprise a tip retention insert which may use either a pair of plates or a plurality of ball bearings to retain the dental syringe tips. An alternate embodiment of a valve may comprise features intended to reduce the force necessary to actuate the valve. A metering screw and/or flow-control groove with increasing depth may control of flow through the valve.

Embodiments of the invention may comprise a flow regulating valve comprising a body defining a flow passageway, a piston extending through the flow passageway and defining an axis, a spring configured to apply a spring force on the piston in a first direction along the axis, a seating surface of at least one of the piston and the body which may comprise a first sloped surface, and an opposing seating surface releasably sealable against the seating surface by the spring force and substantially blocking the flow passageway. Additionally, the seating surface and the opposing seating surface may be cooperatively configured to partially release the opposing seating surface from the seating surface when a first opposing force is applied to displace the piston in a second direction, substantially opposite to the first direction, to thereby partially open the flow passageway. When a second opposing force, which is larger than the first opposing force, is applied, the opposing seating surface may completely release from the seating surface to thereby further open the flow passageway.

Alternate embodiments of flow regulating valves comprise a body defining a flow passageway, a flow-control seal positioned within the flow passageway, a flow passageway end seal positioned within the flow passageway; and a piston defining a flow-control groove extending through the flow passageway, the flow passageway end seal, and the flow-control seal, the piston defining a first direction and a second direction of an axis, wherein the flow passageway end seal is positioned in the second direction from the flow-control seal. A fluid supply conduit is in fluid communication with a first portion of the flow passageway defined between the flow control seal and the flow passageway end seal, wherein the fluid supply conduit is configured to provide a fluid flow applied at the perimeter of the piston in the first portion of the flow passageway. A fluid outlet conduit may be in fluid communication with a second portion of the flow passageway, and a spring positioned in a cavity or other force means may be configured to apply a force on the piston in the first direction (outward) along the axis of travel. In some embodiments the force means comprises a fluid source configured to supply a fluid force to the piston.

The flow-control seal contacts the body and the piston and thereby separates the first portion and the second portion of the flow passageway to substantially prevent fluid communication between the first portion and the second portion of the flow passageway when the piston is in a first position wherein the flow-control groove is displaced from the flow-control seal in the first direction. When the piston is displaced in the second direction (inward), substantially opposite to the first direction to a second position, the flow-control groove extends at least partially beyond the flow-control seal in both the first and second directions, whereby the fluid supply conduit is in fluid communication with the fluid outlet conduit through the first portion and the second portion of the flow passageway. A second flow passageway end seal may be configured to substantially prevent fluid from escaping out of the flow passageway in the first direction. The flow-control groove may be configured to permit increasing flow of fluid through the valve as the piston is displaced in the second direction. In some embodiments at least a portion of the piston at the flow-control groove may define a plurality of cross-sections perpendicular to the axis of the piston which generally decrease in area from the farthest portion of the flow-control groove in the second direction towards the first direction until a maximum groove depth is reached, which may allow for more precise flow control.

A first centering sleeve may be positioned within the flow passageway with the piston extending through the first centering sleeve to thereby substantially prevent movement of the piston other than in the first and second direction. The first centering sleeve may be positioned in the first portion of the flow passageway, and the first centering sleeve comprises an inlet aperture through which fluid communication between the fluid supply conduit and the flow-control groove occurs when the piston is displaced in the second direction. A second centering sleeve may be positioned within the second portion of the flow passageway, wherein the second centering sleeve comprises an outlet aperture through which fluid communication between the flow-control groove and the fluid outlet conduit occurs when the piston is displaced in the second direction.

The flow control valve may comprise features intended to reduce the actuation force necessary to operate the flow control valve. For example, the cavity may be in communication with a cavity pressure, wherein the cavity pressure is less than the pressure in the fluid supply conduit such as when the cavity pressure is ambient air pressure. In particular, the cavity may be in communication with ambient air pressure through a pressure relief conduit. Further, the fluid supply conduit may be substantially out of fluid communication with the distal ends of the piston. Further, the total area of the piston perpendicular to the axis which is exposed to force from the fluid in the second direction may be greater than, less than, or equal to the total area of the piston perpendicular to the axis which is exposed to force from the fluid in the first direction.

The flow control valve may further comprise a first retaining member, the first retaining member extending at least partially through the body and at least indirectly contacting the first centering sleeve to thereby restrain movement of the first centering sleeve and the flow-control seal at least in the first direction. The flow control valve may also comprise a second retaining member, the second retaining member coupling to the piston in the cavity, whereby movement of the piston in the first direction is at least partially restrained by indirect contact between the second retaining member and the first retaining member through at least the centering sleeve and the flow-control seal.

A method of controlling a flow of fluid is also provided. The method may include providing a valve comprising a piston defining a flow-control groove and extending through a flow passageway defined in a body and a flow passageway end seal and a flow-control seal positioned within the flow passageway, wherein the flow-control seal separates the flow passageway into a first portion, defined between the flow-control seal and the flow passageway end seal, and a second portion and providing a force means configured to apply a force to the piston in a first direction along an axis of travel defined by the piston. The method may further comprise displacing the piston in a second direction along the axis of travel opposite to the first direction to bring the first portion and the second portion of the flow passageway into fluid communication through the flow-control groove and thereby allow fluid to flow through the valve and releasing the piston, whereby the force means displaces the piston including the flow-control groove in the first direction and thereby prevents fluid communication between the first portion and the second portion of the flow passageway and prevents flow of fluid through the valve.

In some embodiments the fluid supply conduit may comprise a metering screw, the metering screw comprising a cylindrical end portion which is configured to be received by a metering cavity in the body, the metering cavity comprising a cylindrical end cavity. The cylindrical end portion is moveable from an extended position to a retracted position, wherein when the cylindrical end portion is in the extended position, the metering screw occupies a first occupied volume of the metering cavity, and wherein when the cylindrical end portion is in the retracted position, the metering screw occupies a second occupied volume of the metering cavity. The second occupied volume may be less than the first occupied volume, and the fluid supply conduit is in fluid communication with the first portion of the flow passageway when the cylindrical end portion is in the extended position and the retracted position. Alternate embodiments of metering screws are also provided. In one such embodiment the metering screw comprises a threaded portion defining a first end rotatably operable by a user and a second end defining a cavity, and a compressible cylindrical end portion received within the cavity defined by the second end of the threaded portion and extending therefrom along an axis. The compressible cylindrical end portion may define a spherical end. There is further provided, a fluid flow metering system comprising a metering screw configured to be received by a body defining a metering cavity. The fluid flow metering system comprises a threaded portion configured to screw into a threaded receiving portion of the metering cavity, and a compressible cylindrical end portion coupled to the threaded portion and moveable along an axis between an extended position and a retracted position in a cylindrical end cavity defined by the metering cavity. When the compressible cylindrical end portion is in the extended position, the compressible cylindrical end portion is compressed along the axis and radially expanded to substantially seal against the cylindrical end cavity to substantially prevent flow of a fluid therethrough. Further, when the compressible cylindrical end portion is in the retracted position, the compressible cylindrical end portion is at least partially out of contact with the cylindrical end portion to allow flow of the fluid therethrough.

In additional embodiments of the invention, a replaceable valve cartridge for a dental syringe may comprise a housing which contains one or more valves, and a seal for sealing an axially inserted dental syringe tip.

Further embodiments of the invention may include a replaceable tip retention insert for a dental syringe, comprising a housing at least partially defining a cavity configured for insertion of a dental syringe tip, one or more clamping members moveably positioned around the cavity, one or more springs configured to bias the clamping members at least partially into the cavity, and at least one releasable cartridge retainer configured to releasably hold the replaceable tip retention insert in a head of the dental syringe. The clamping members may comprise a first plate and a second plate. Alternatively, the clamping members may comprise a plurality of ball bearings, wherein the springs provide a radially inwardly directed force on each of the spheres.

Additional further embodiments of the invention may comprise a seal for sealing an axially inserted dental syringe tip configured to direct a first fluid through a first fluid path, direct a second fluid through a second fluid path, prevent bleed-over of the first fluid into the second fluid path, and prevent bleed-over of the second fluid into the first fluid path. Such embodiments may comprise a first channel defined between a first ring of a first elastic portion and a second ring of a second elastic portion, and a bleed path. The first channel may be configured to be in fluid communication with the bleed path, and configured to permit any of the first fluid and the second fluid which reaches the first channel to exit through the bleed path.

Alternate embodiments of the invention may comprise a system to remove a residual liquid from a tip of a dental syringe having supplies of a liquid and a second fluid thereto. These embodiments may comprise a body defining a cavity comprising an inlet, an outlet, and an outlet sealing surface, a moveable stopper located within the cavity and configured to bias against the outlet sealing surface by the second fluid so as to at least partially seal the outlet, and a plunger configured to move in a first direction along a longitudinal axis of the plunger to displace the stopper from the outlet sealing surface and further configured to move in a second direction, substantially opposite to the first direction, such that the outlet is in fluid communication with the tip of the dental syringe.

Other embodiments of the invention may comprise a method of removing a residual liquid from a tip of a dental syringe having supplies of a liquid and a second fluid thereto. Such embodiments may comprise actuating a single actuator to dispense the liquid from the tip of the dental syringe and automatically dispensing the second fluid out of the tip of the dental syringe following the dispensing of the liquid. The dispensing of the second fluid may substantially remove the residual liquid from the tip of the dental syringe.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 2F:
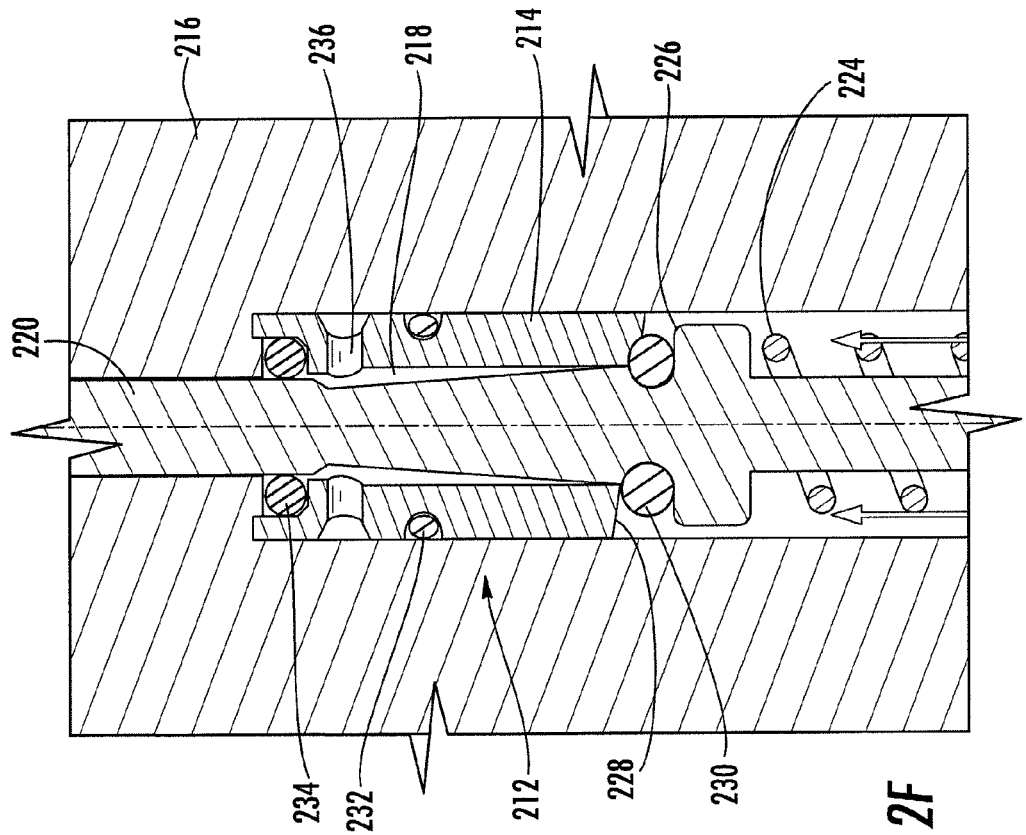
FIG. 2F illustrates an enlarged portion of the flow regulating valve of FIG. 2.
Figure 2:
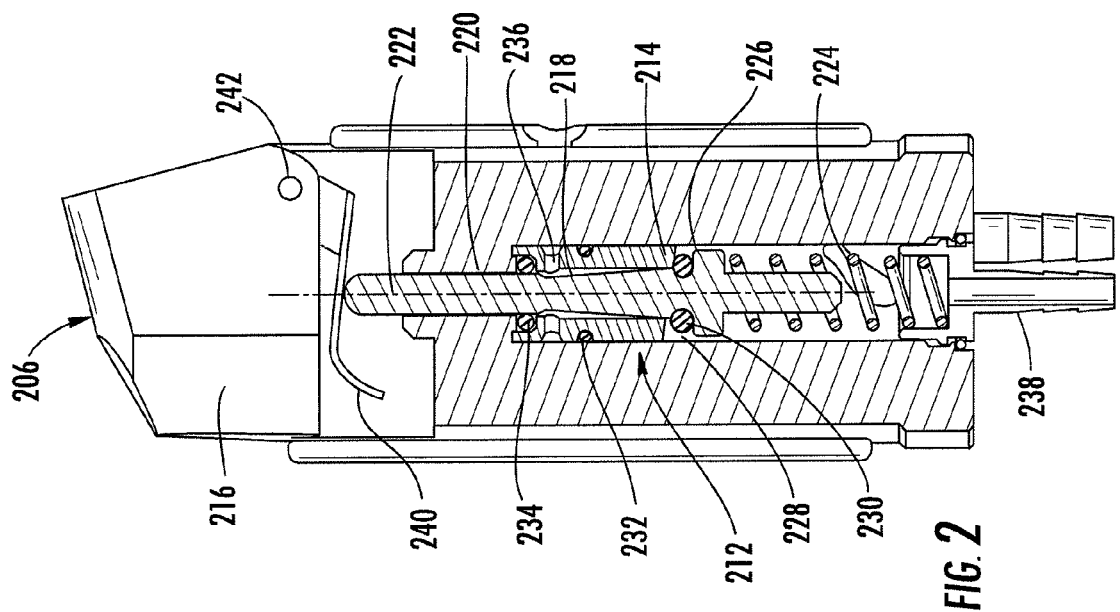
FIG. 2 illustrates a cross-sectional view of an embodiment of a flow regulating valve having a plug serving as a body with a sloped seating surface within a replaceable valve cartridge for a dental syringe.
Figure 2G:
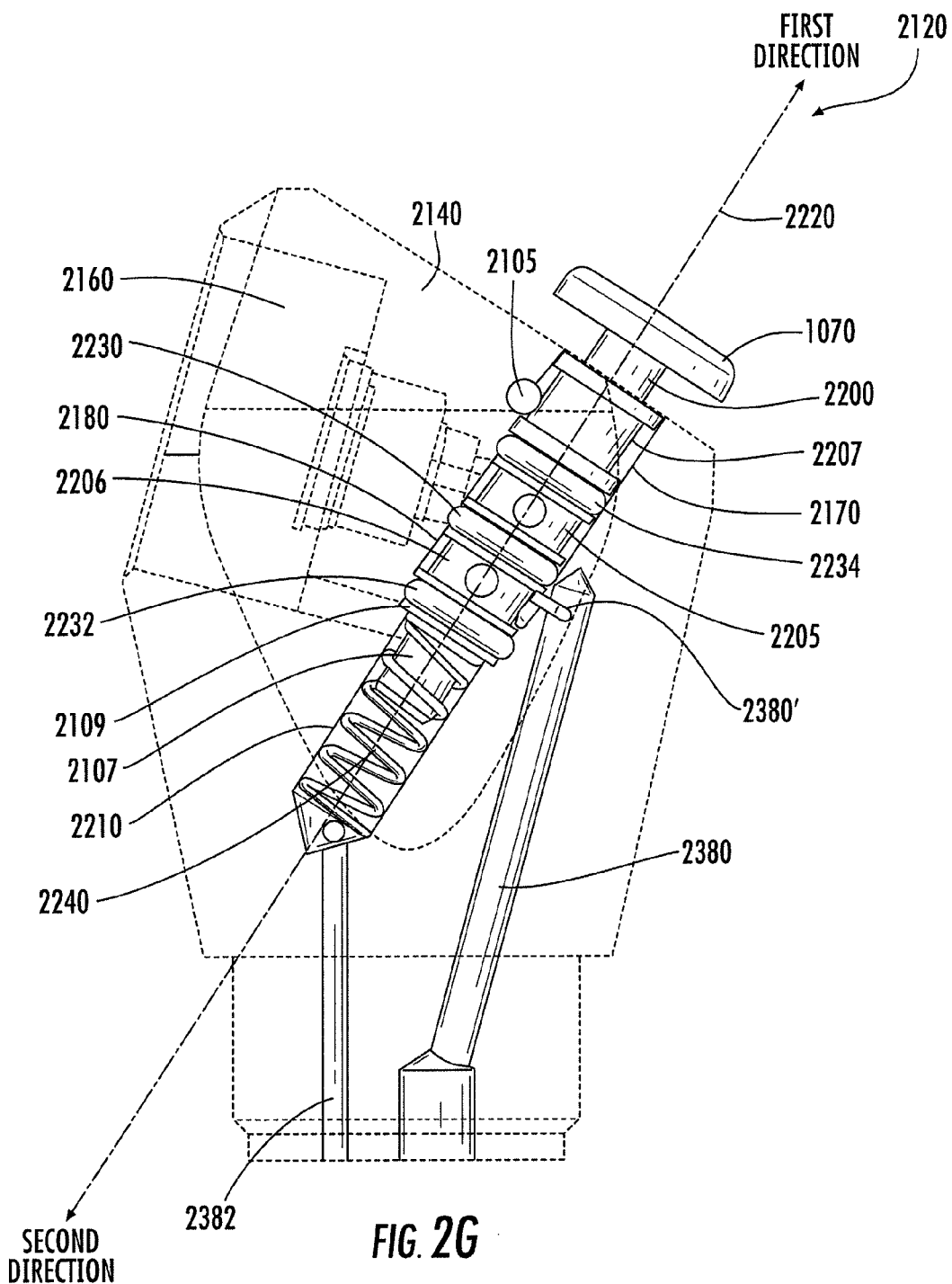
FIG. 2G illustrates an alternate embodiment of a flow regulating valve.
Figure 2H:
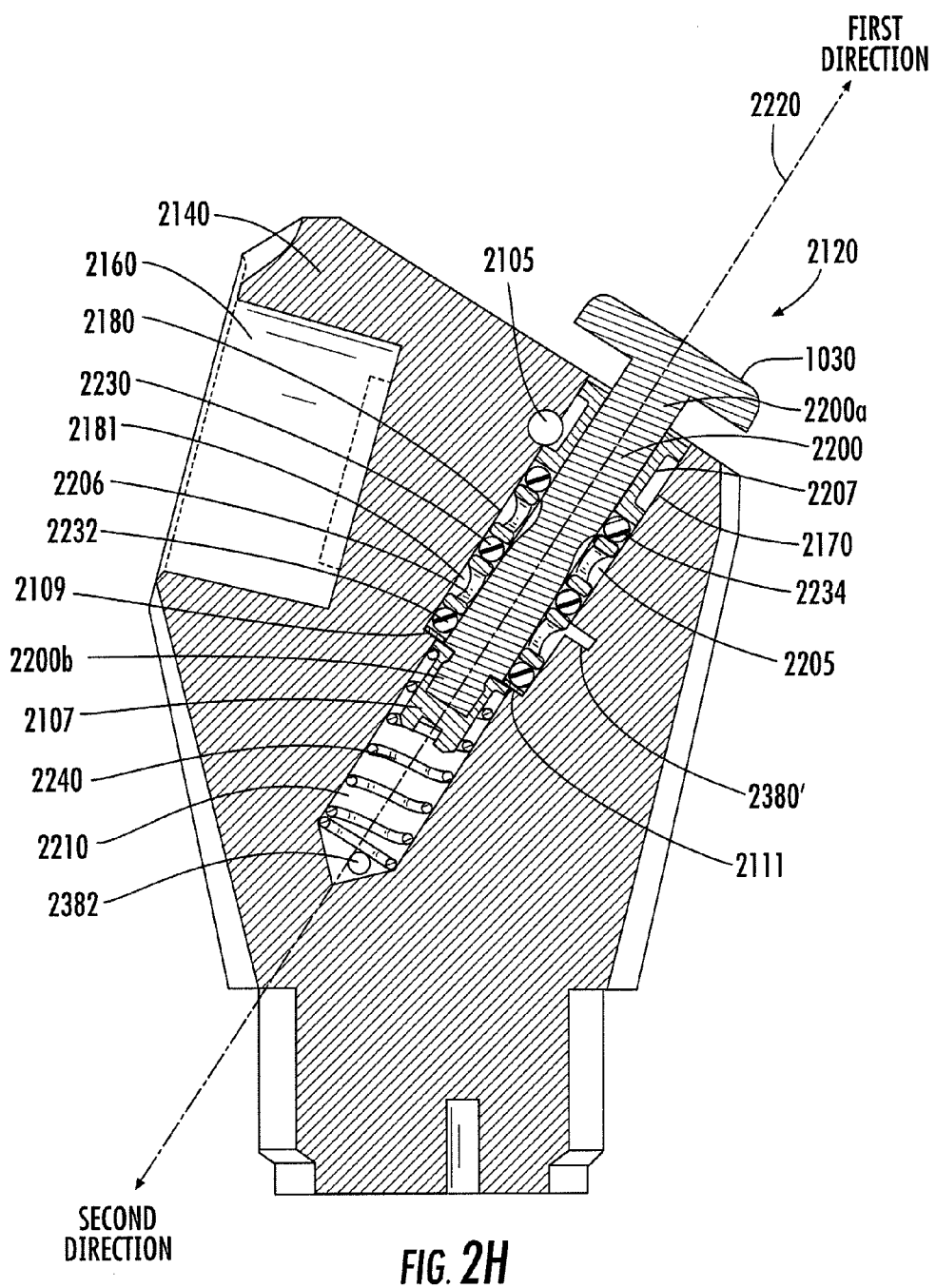
FIG. 2H illustrates an alternate cross-sectional view of the flow regulating valve of FIG. 2G.
Figure 2K:
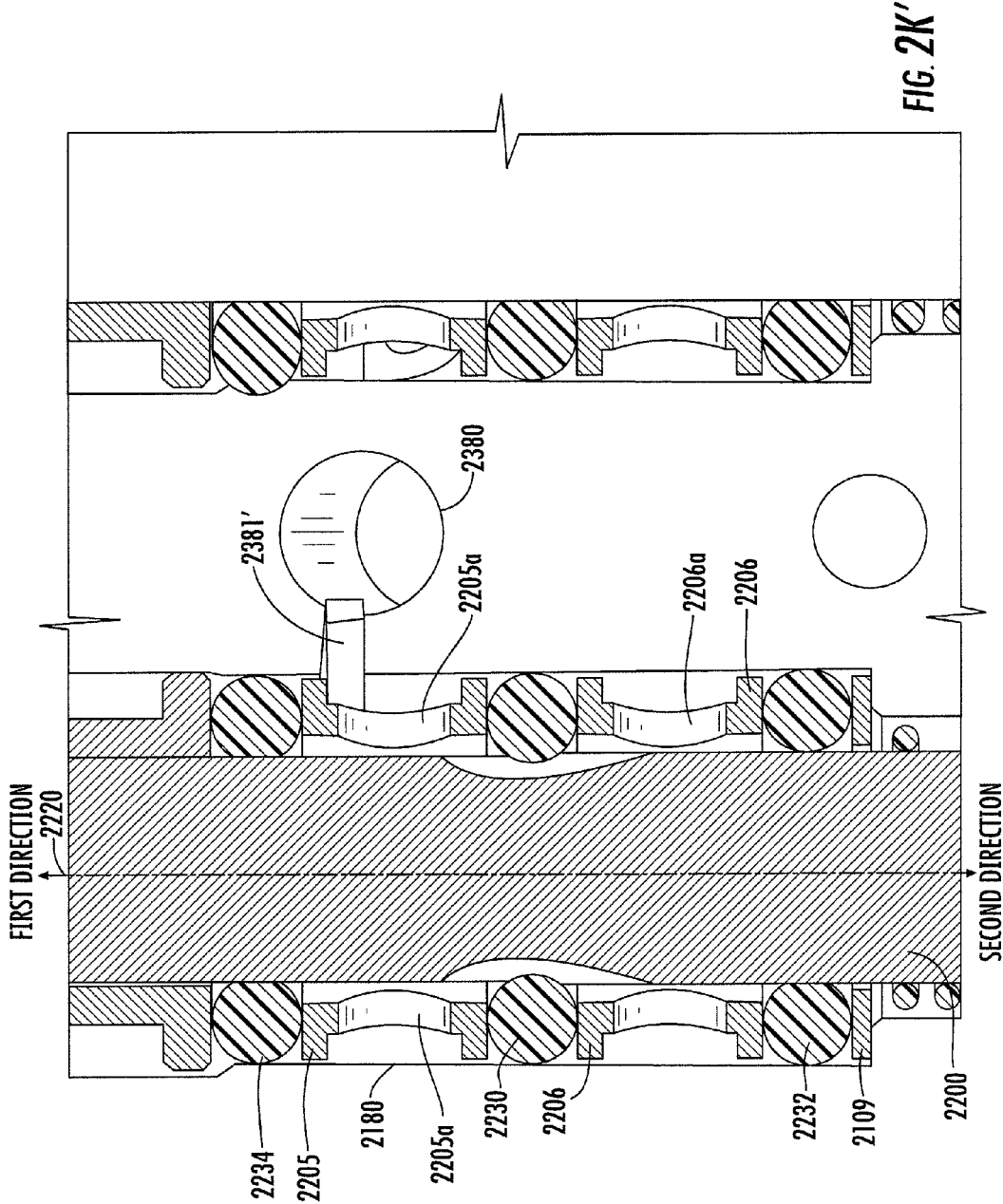
FIG. 2K illustrates an enlarged alternate cross-sectional view of the flow regulating valve of FIG. 2G in the second position.
Figure 2L:
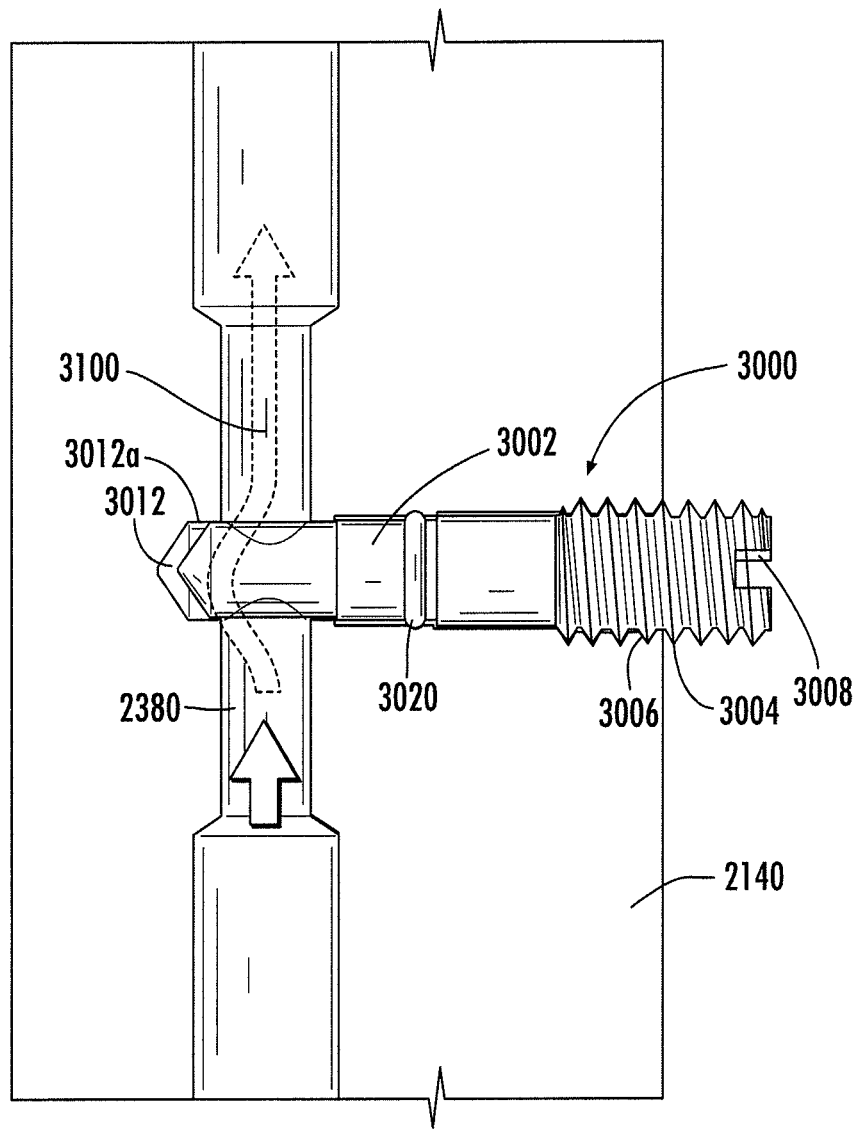
FIG. 2A illustrates a schematic representation of an embodiment of a flow regulating valve having a body with a sloped seating surface in a closed position.
FIG. 2B illustrates a schematic representation of the embodiment of a flow regulating valve of FIG. 2A having a body with a sloped seating surface in a partially open position.
FIG. 2C illustrates a schematic representation of the embodiment of a flow regulating valve of FIG. 2A having a body with a sloped seating surface in a fully open position.
FIG. 2D illustrates a schematic representation of an embodiment of a flow regulating valve having a piston with a sloped seating surface in a closed position.
FIG. 2E illustrates a schematic representation of an embodiment of a flow regulating valve having a first sloped seating surface and a second sloped opposing seating surface in a closed position.
FIG. 2I illustrates a modified cross-sectional view of the flow regulating valve of FIG. 2G from an alternate perspective in a first position, which substantially prevents flow.
FIG. 2J illustrates a modified cross-sectional view of the flow regulating valve of FIG. 2G from an alternate perspective in a second position, which allows flow.
Figure 2M:
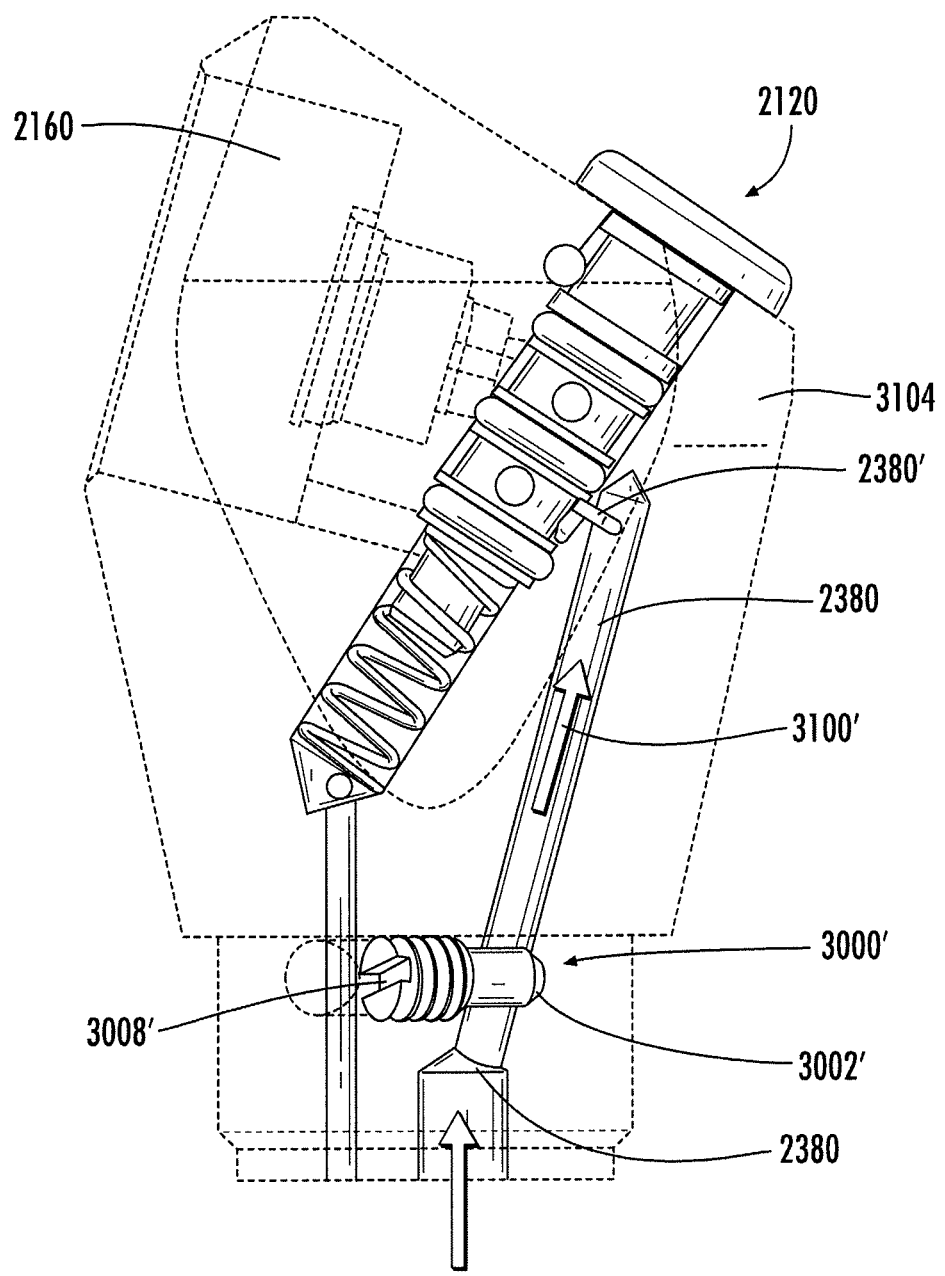
Figure 2N:
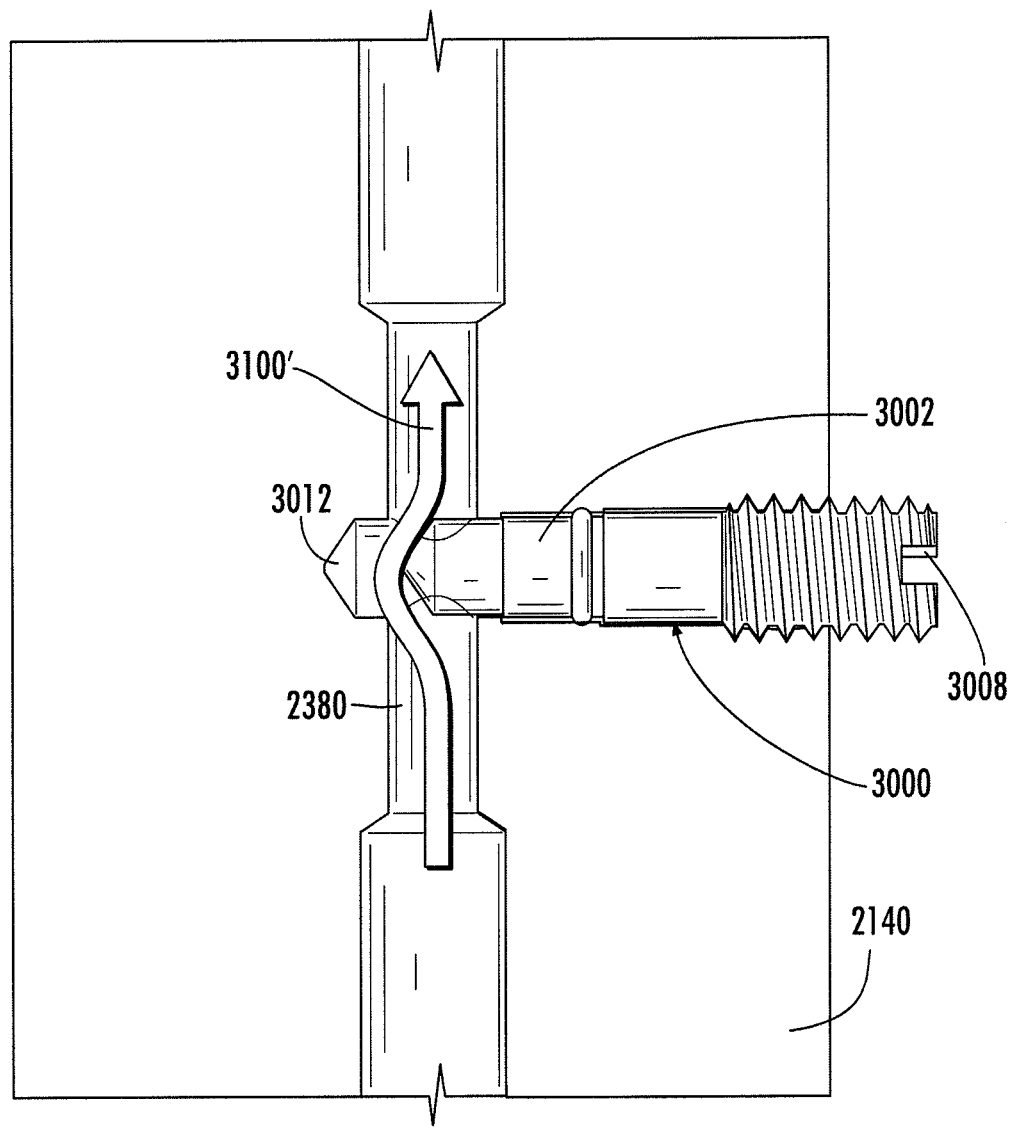

FIG. 2K' illustrates an enlarged alternate cross-sectional view of the flow regulating valve of FIG. 2G in the second position, including the fluid outlet conduit;

FIG. 2K" illustrates a piston comprising the flow regulating valve of FIG. 2G;

FIG. 2K'" illustrates a cross-sectional view along the length of the piston of FIG. 2K";

FIG. 2K"" illustrates a an enlarged view of the section B from FIG. 2K'" showing a groove defined in the piston;

FIG. 2K'"" illustrates a cross sectional view through the groove from FIG. 2K"";

FIG. 2L illustrates a cross-sectional view of a metering screw in an extended position which allows a relatively small flow;

FIG. 2M illustrates a perspective view of an embodiment of a metering screw of with a compressible cylindrical end portion in the head portion of a dental syringe;

FIG. 2N illustrates the metering screw of FIG. 2L in a retracted position which allows a relatively large flow;

FIG. 2O illustrates an alternate perspective of the metering screw of FIG. 2M in the head portion of a dental syringe.

Figure 3A:
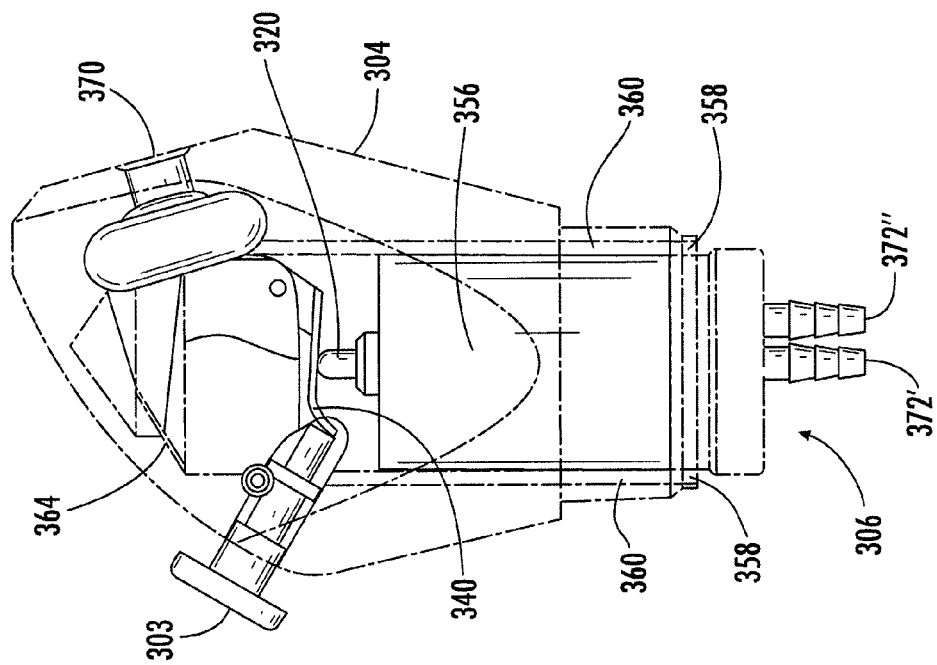
Figure 3:
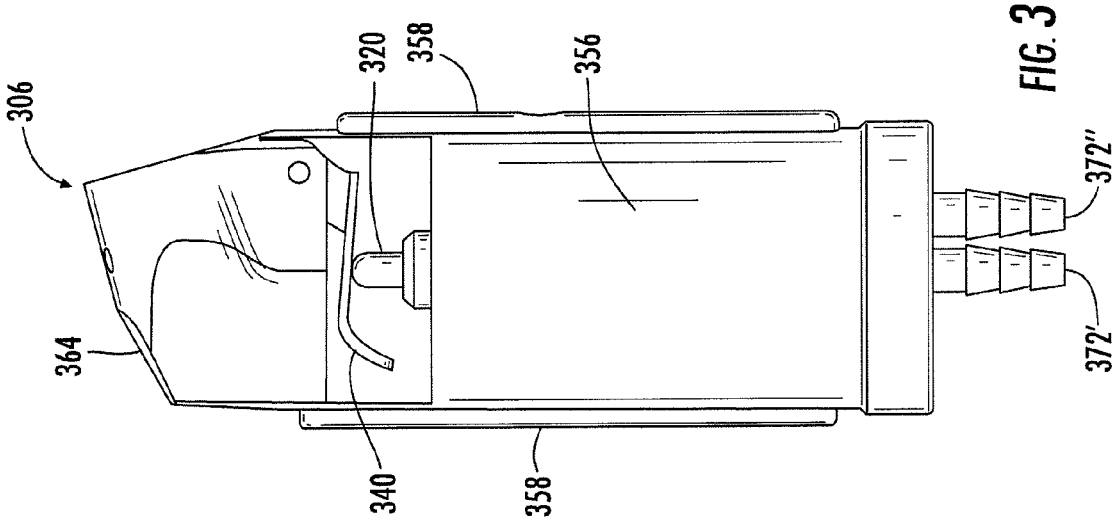
Figure 3B:
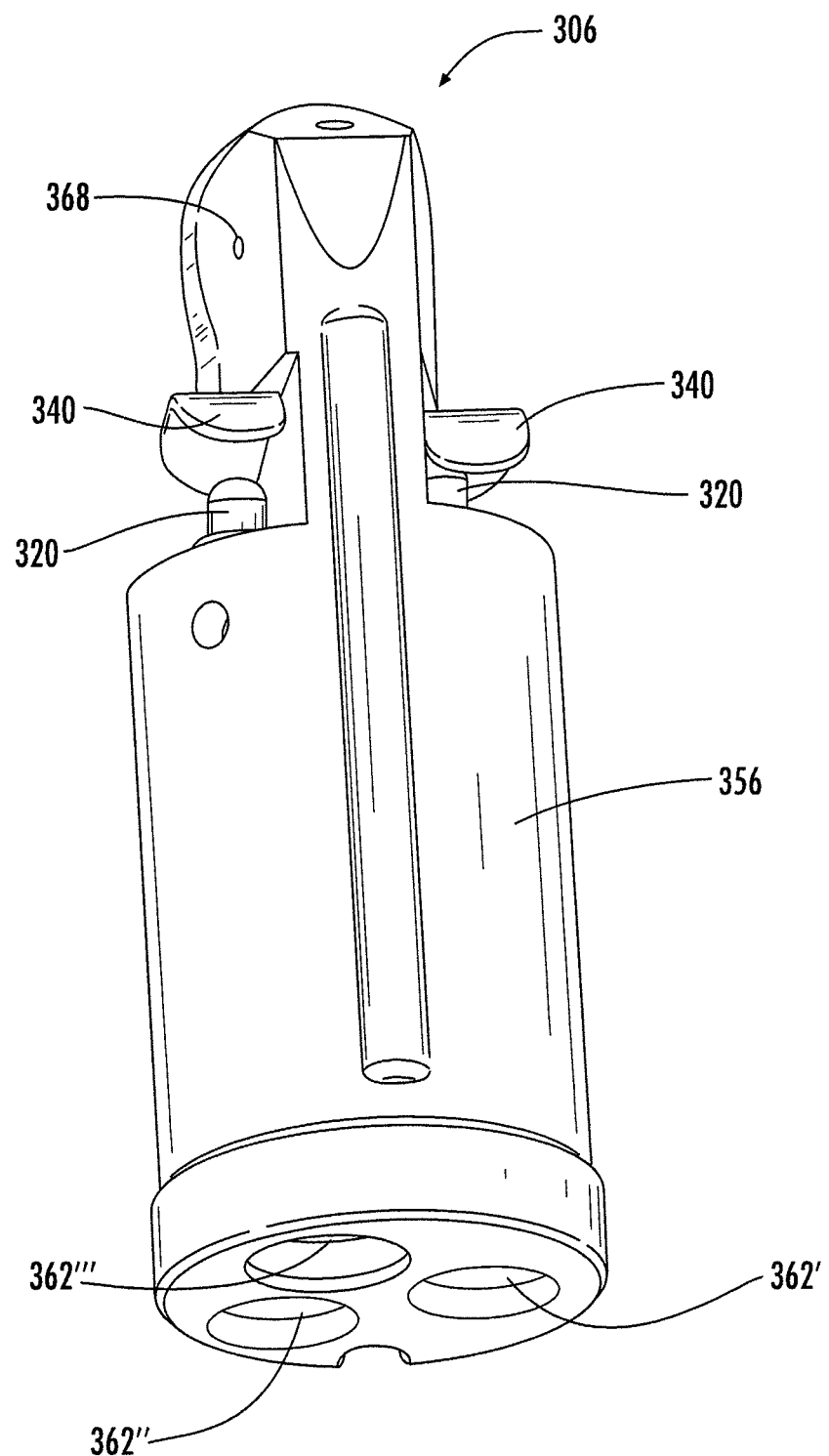
Figure 3C:
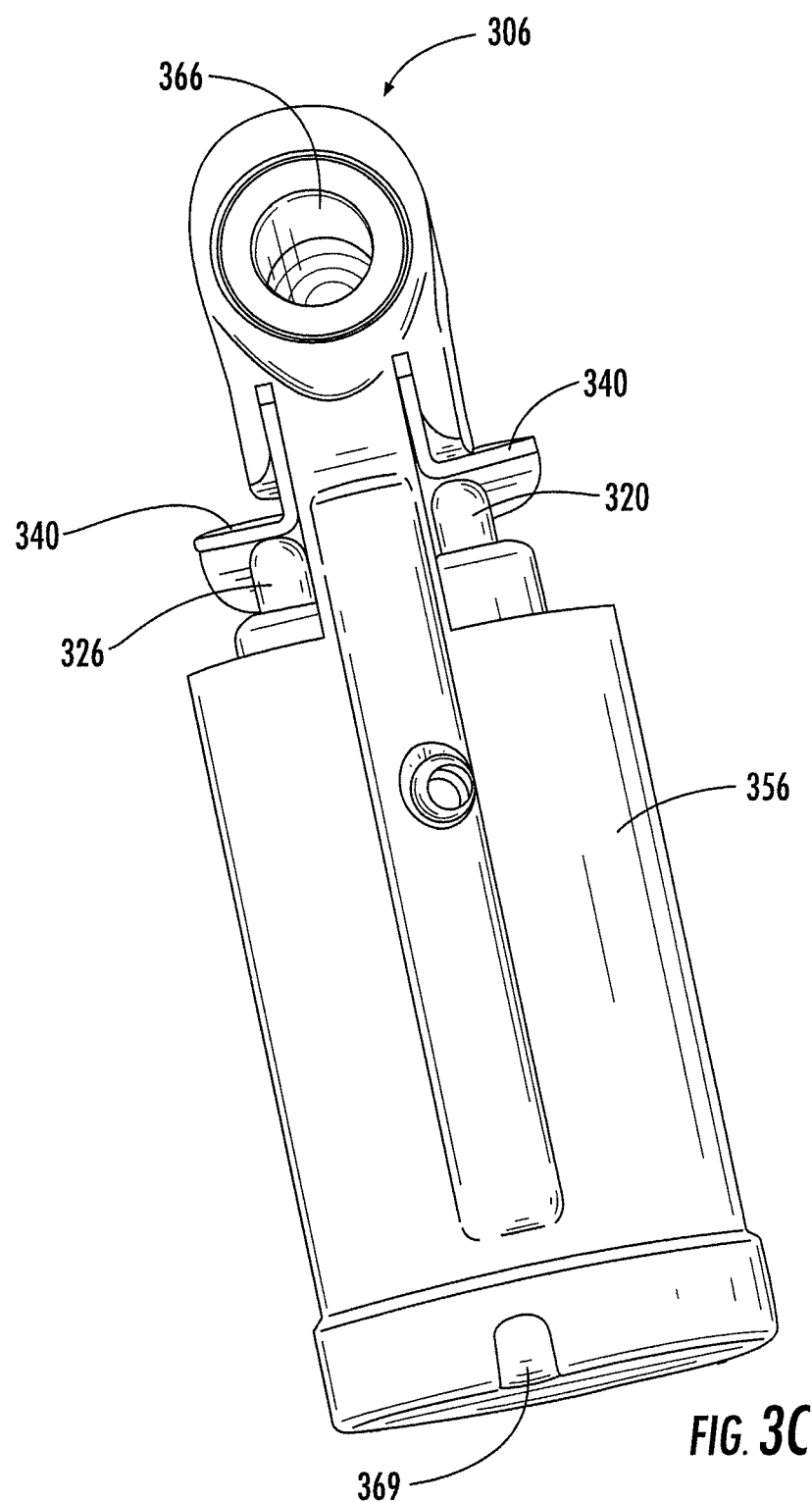
Figure 4A:
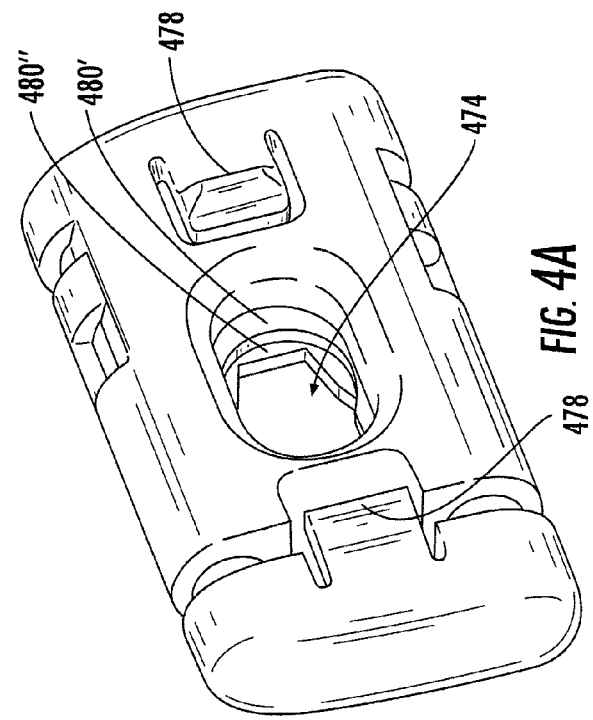
Figure 4B:
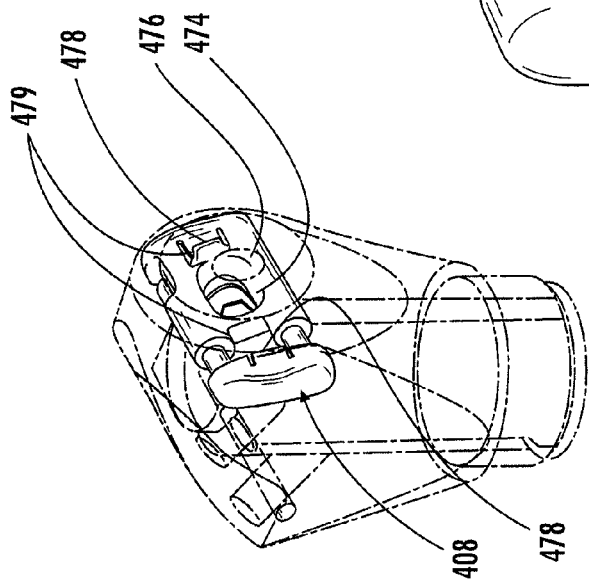
Figure 4:
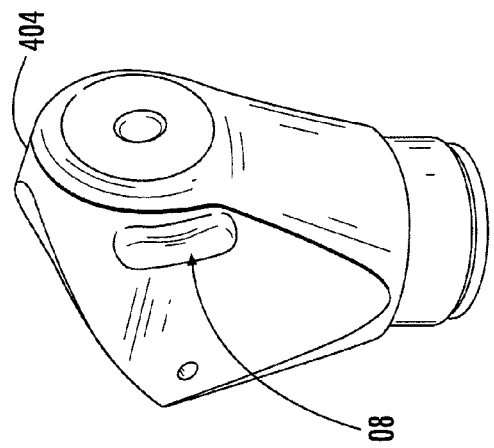
Figure 4C:
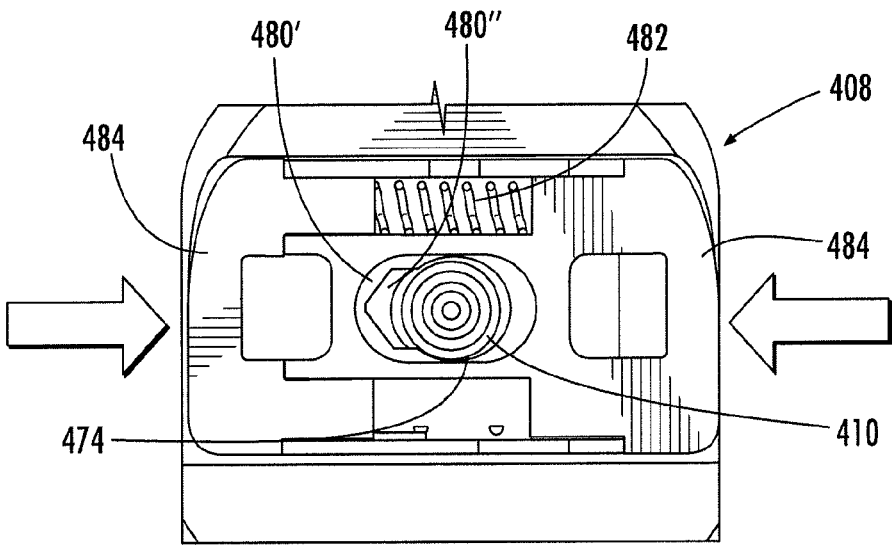
Figure 4D:
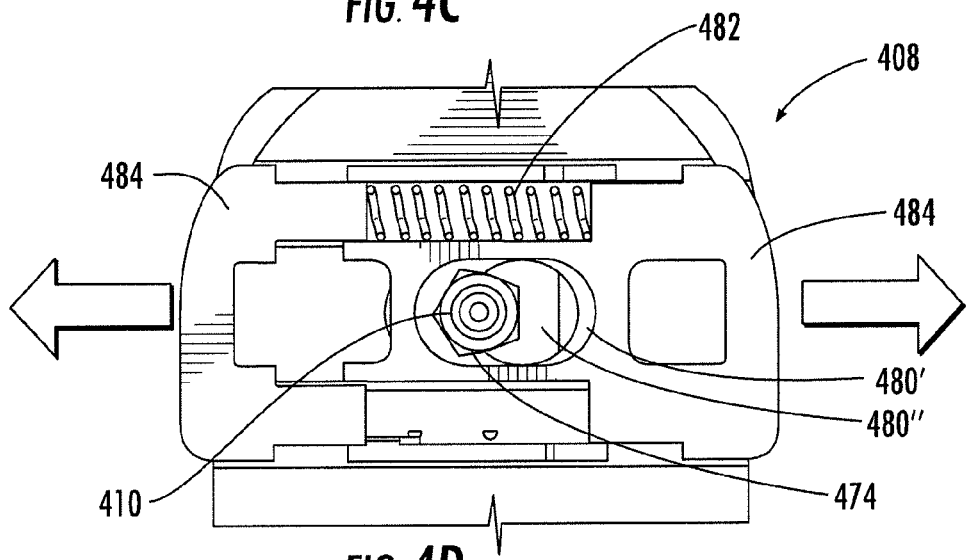
Figure 4E:
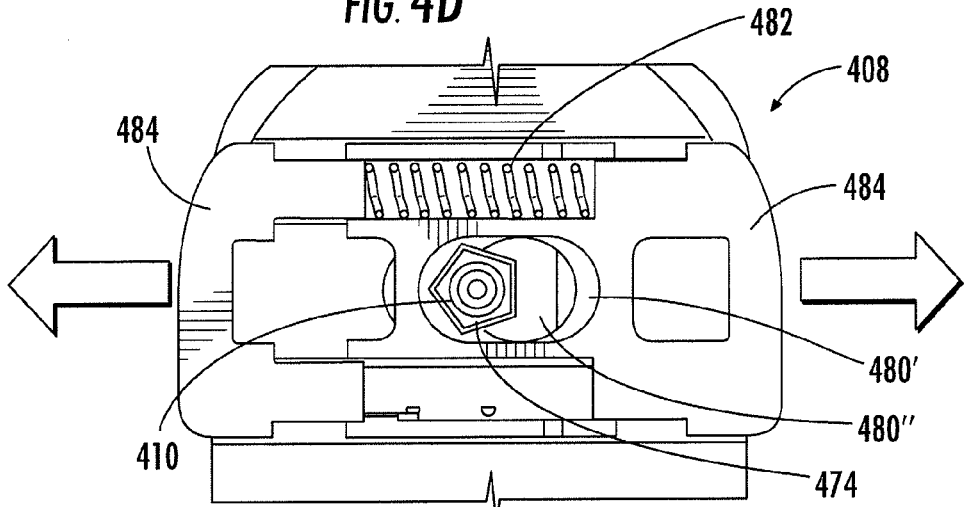
Figure 4F:
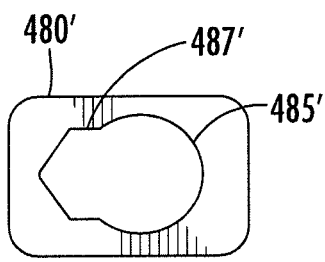
Figure 4G:
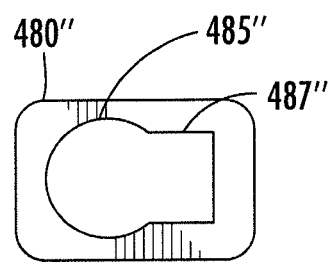
Figure 4H:
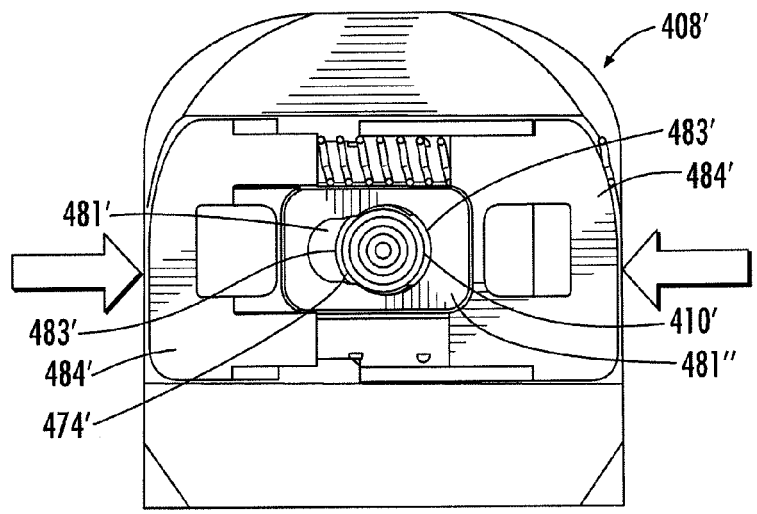
Figure 4I:
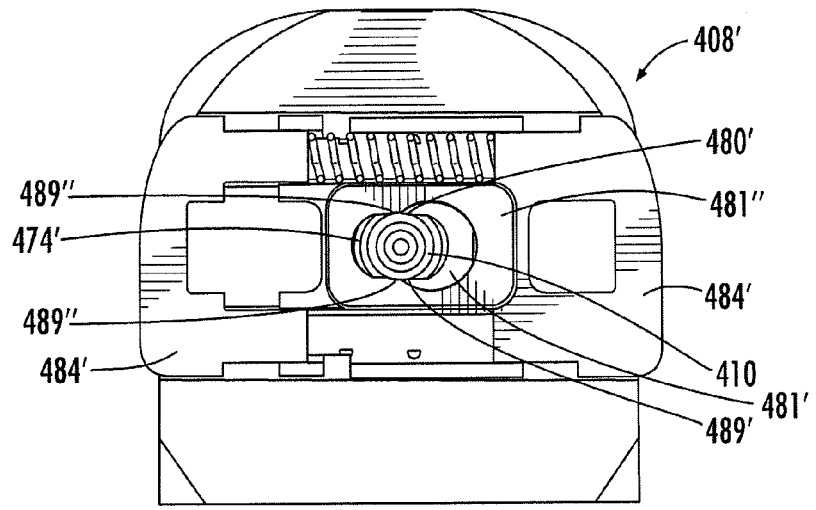
Figure 4J:
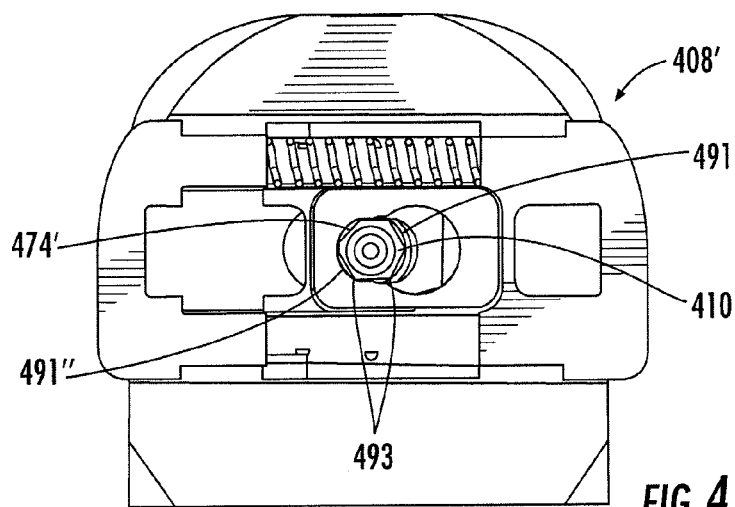
Figure 4K:
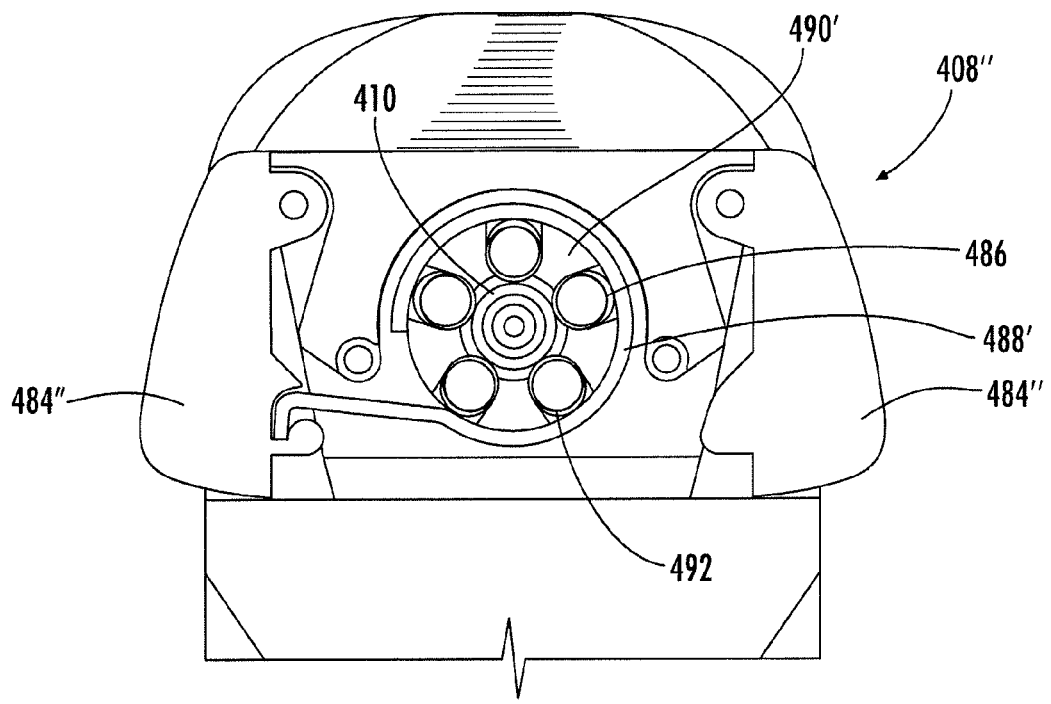
Figure 4L:
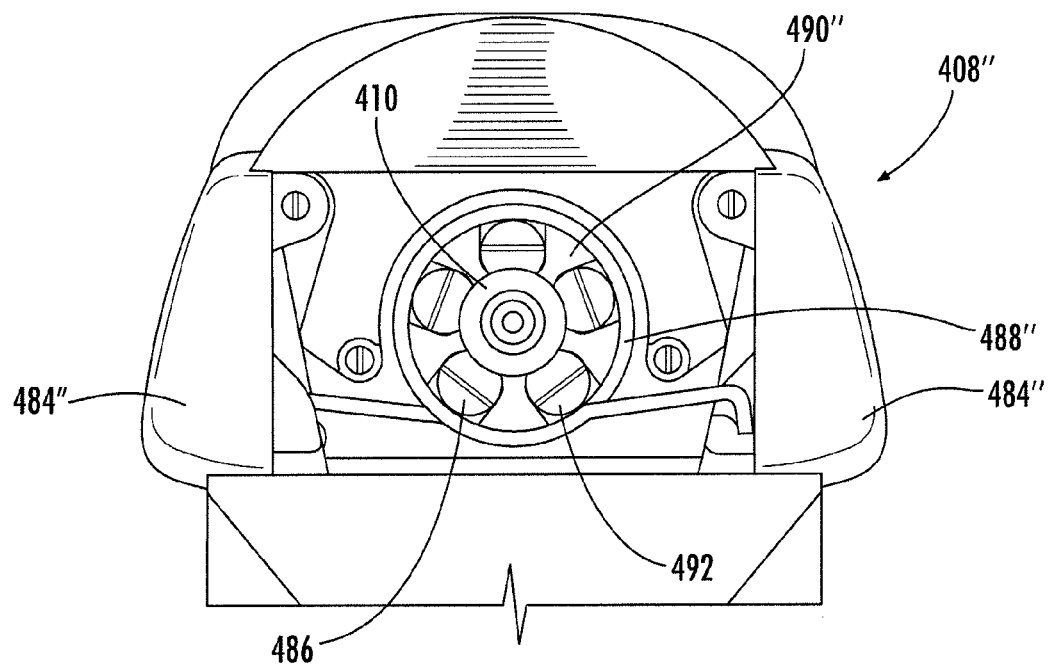
Figure 5A:
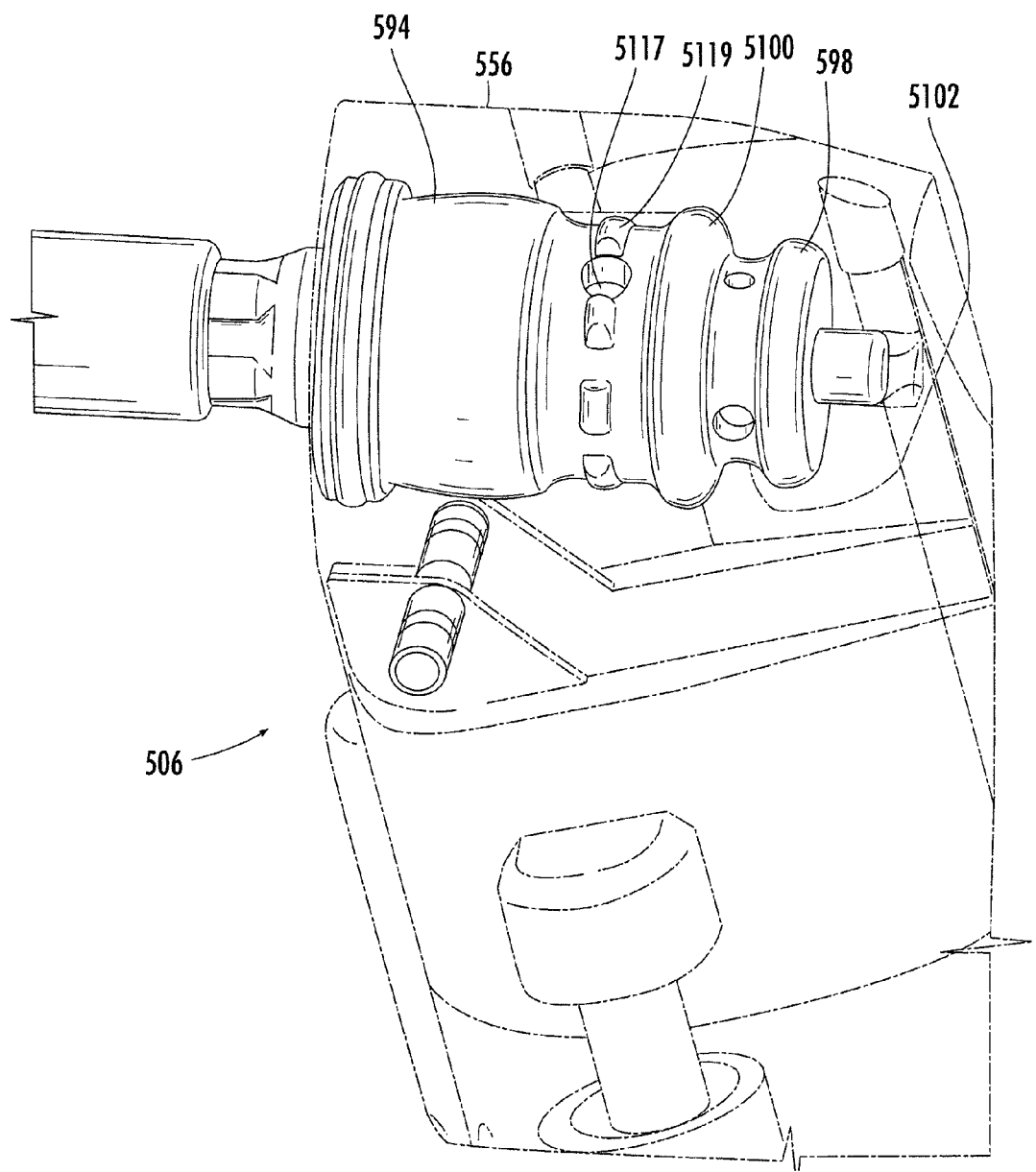
Figure 5C:
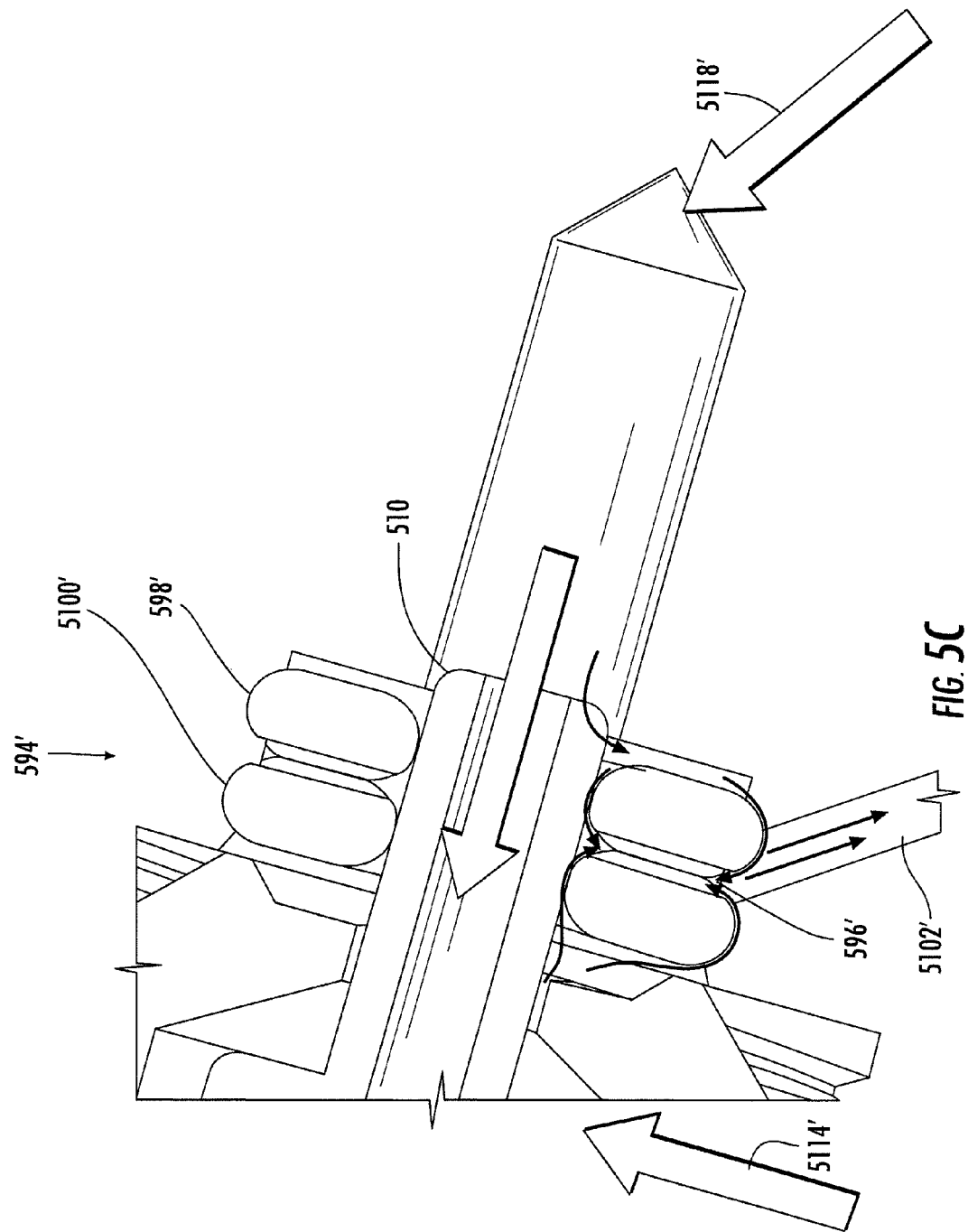
Figure 6D:
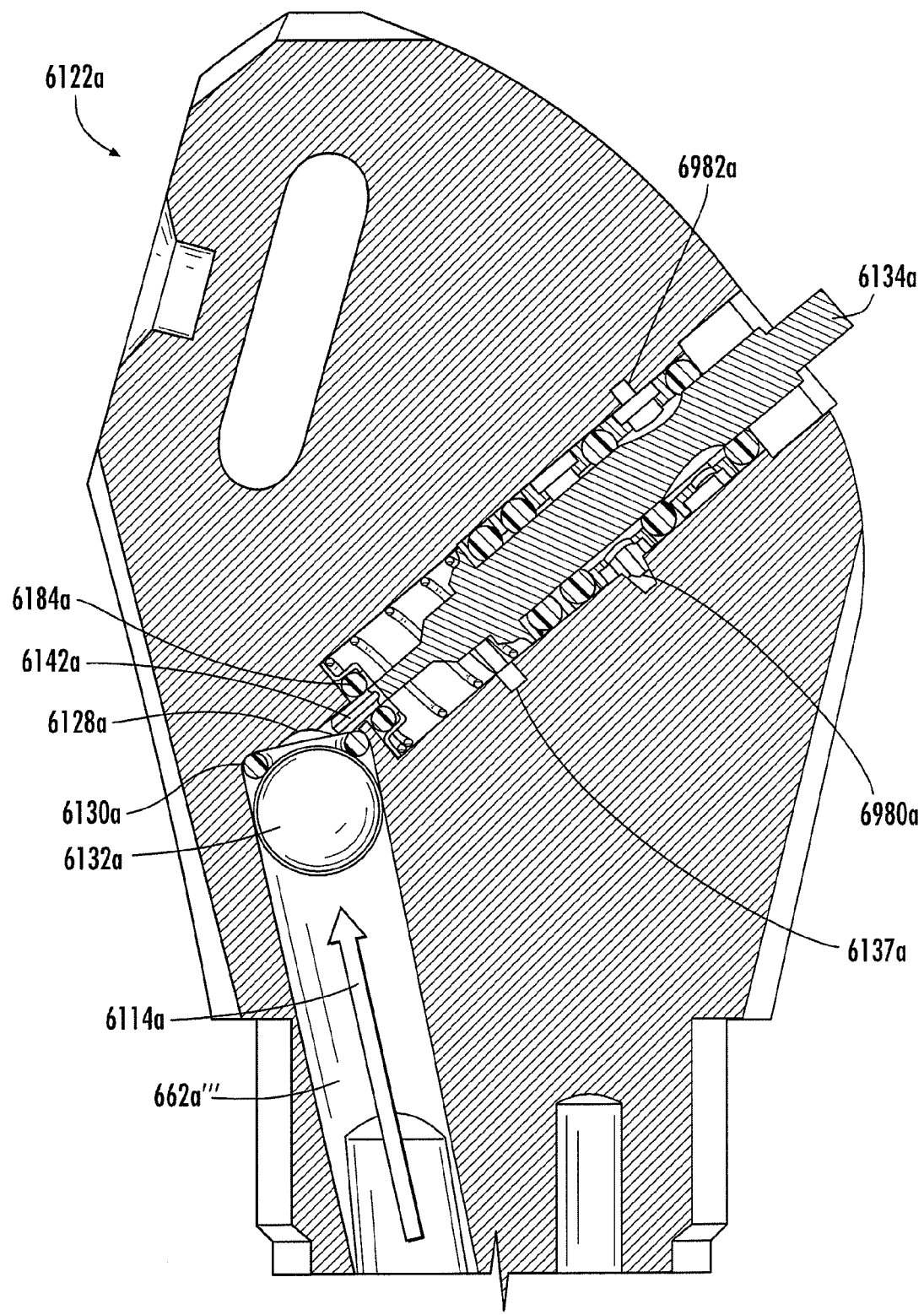
Figure 7A:
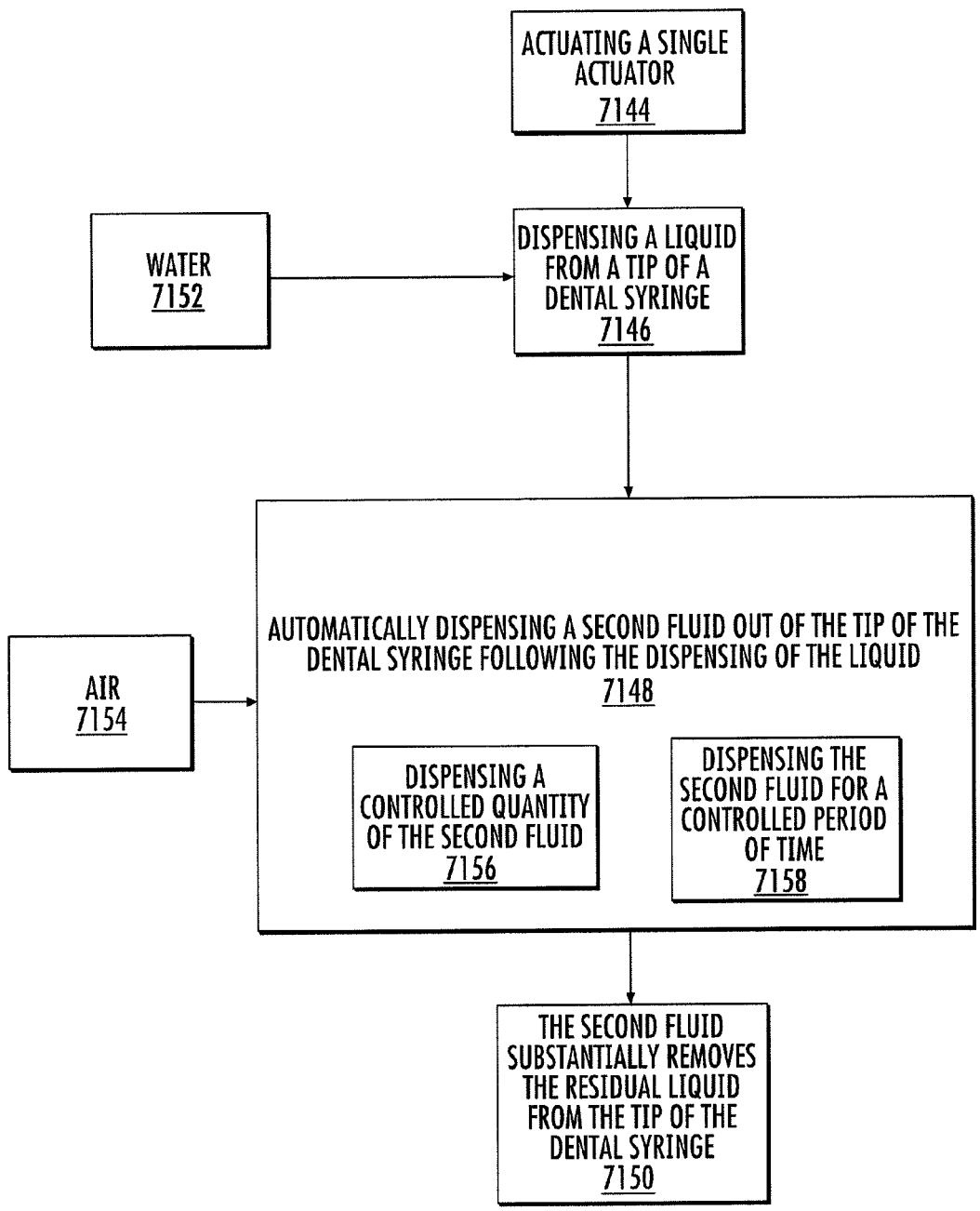
Figure 7B:
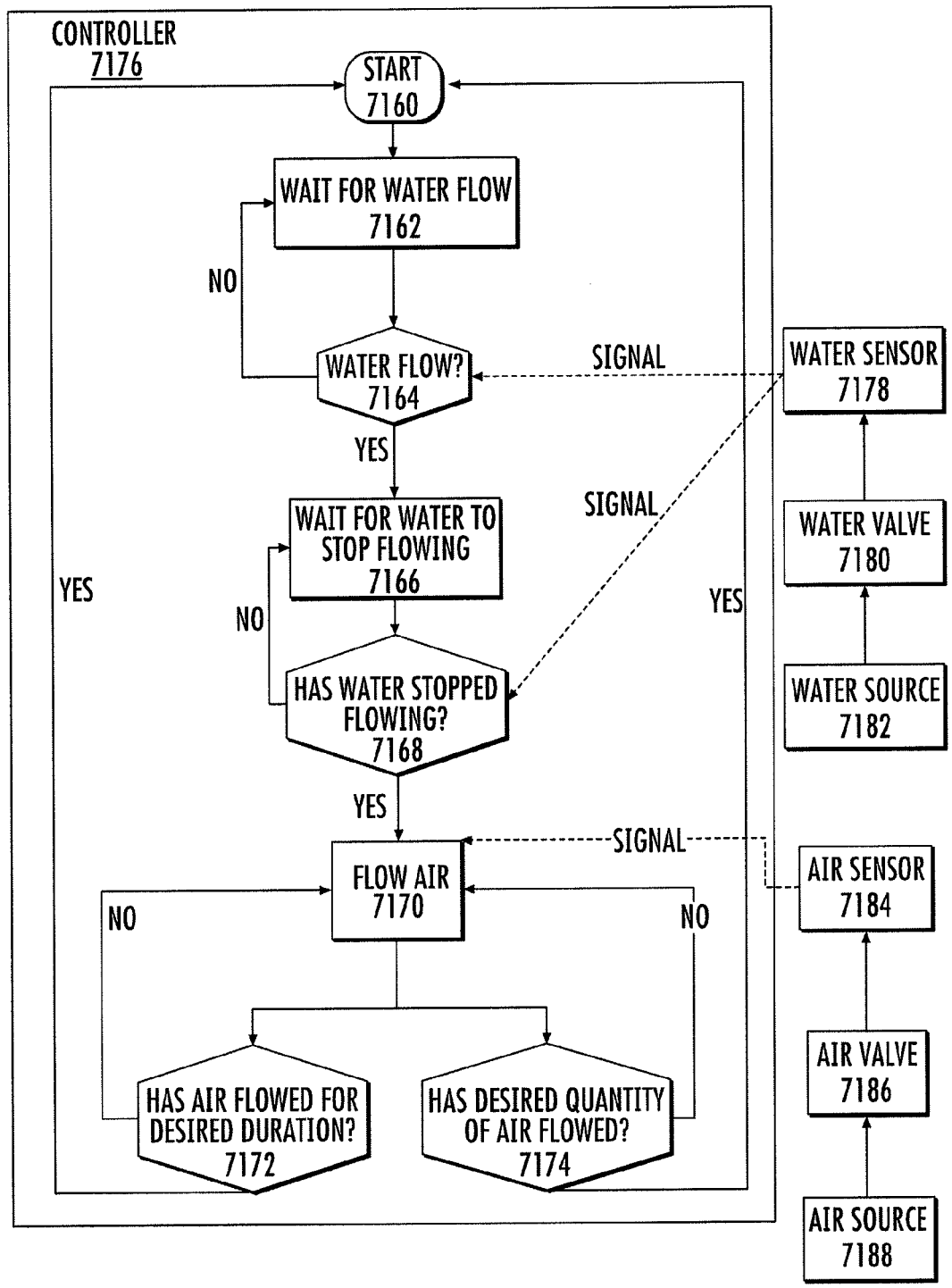

FIG. 3 illustrates a side view of an embodiment of a replaceable valve cartridge;

FIG. 3A illustrates a side view of the replaceable valve cartridge of FIG. 3 positioned within a head portion of a dental syringe shown in partial transparency;

FIG. 3B illustrates a perspective view of the bottom and back of an embodiment of a replaceable valve cartridge;

FIG. 3C illustrates a perspective view of the front of the replaceable valve cartridge of FIG. 3B;

FIG. 4 illustrates a perspective view of the side and front of an embodiment of a head portion of a dental syringe having a tip retention insert;

FIG. 4A illustrates a perspective view of a tip retention insert of FIG. 4;

FIG. 4B illustrates a perspective view of the side and front of the head portion of FIG. 4 wherein the head portion is shown in partial transparency;

FIG. 4C illustrates a cross-sectional view of the tip retention insert of FIG. 4 in an open position;

FIG. 4D illustrates a cross-sectional view of the tip retention insert of FIG. 4 in a closed position with a regular dental syringe tip;

FIG. 4E illustrates a cross-sectional view of the tip retention insert of FIG. 4 in a closed position with an indexing dental syringe tip;

FIG. 4F illustrates a front schematic view of a first plate of the tip retention insert of FIG. 4;

FIG. 4G illustrates a front schematic view of a second plate of the tip retention insert of FIG. 4;

FIG. 4H illustrates a cross-sectional view of a tip retention insert with intermediate and distal locking sections in an open position;

FIG. 4I illustrates a cross-sectional view of the tip retention insert of FIG. 4H in a closed position with a regular tip secured therein;

FIG. 4J illustrates a cross-sectional view of the tip retention insert of FIG. 4H in a closed position with an indexing tip locked therein;

FIG. 4K illustrates a cross-sectional view of an additional embodiment of a tip retention insert comprising ball bearings and a spring contacting one button;

FIG. 4L illustrates a modified cross-sectional view of the embodiment of a tip retention insert of FIG. 4K showing comprising ball bearings and a spring;

FIG. 5 illustrates a modified cross-sectional view of a seal for sealing a dental syringe tip in a replaceable valve cartridge;

FIG. 5A illustrates a perspective view of the seal for sealing a dental syringe tip in a replaceable valve cartridge of FIG. 5 with the replaceable valve cartridge shown in partial transparency;

FIG. 5B illustrates a modified cross-sectional view of the seal for sealing a dental syringe tip in a replaceable valve cartridge of FIG. 5 with the replaceable valve cartridge shown in partial transparency;

FIG. 5C illustrates an alternate embodiment of a seal for sealing a dental syringe tip and fluid flow patterns therethrough;

FIG. 6A illustrates a modified cross-sectional view of an embodiment of a system for removing a residual liquid from the tip of a dental syringe and showing the positioning of the elements of the system before a liquid has been dispensed from the dental syringe;

FIG. 6B illustrates a cross-sectional view of the system of FIG. 6A showing the positioning of the elements of the system while the liquid is being dispensed and hence the moveable stopper has been displaced from the outlet sealing surface;

FIG. 6C illustrates a cross-sectional view of the system of FIG. 6A showing the positioning of the elements of the system when the liquid is no longer being dispensed and hence a puff of fluid is being released;

FIG. 6D illustrates a cross-sectional view of an additional embodiment of a system for removing residual liquid from a tip of a dental syringe in which an opening through the plunger defines a flow path;

FIG. 7A illustrates a flow chart of a first method for removing a residual liquid from the tip of a dental syringe; and FIG. 7B illustrates a flow chart of a second method for removing a residual liquid from the tip of a dental syringe.

DETAILED DESCRIPTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
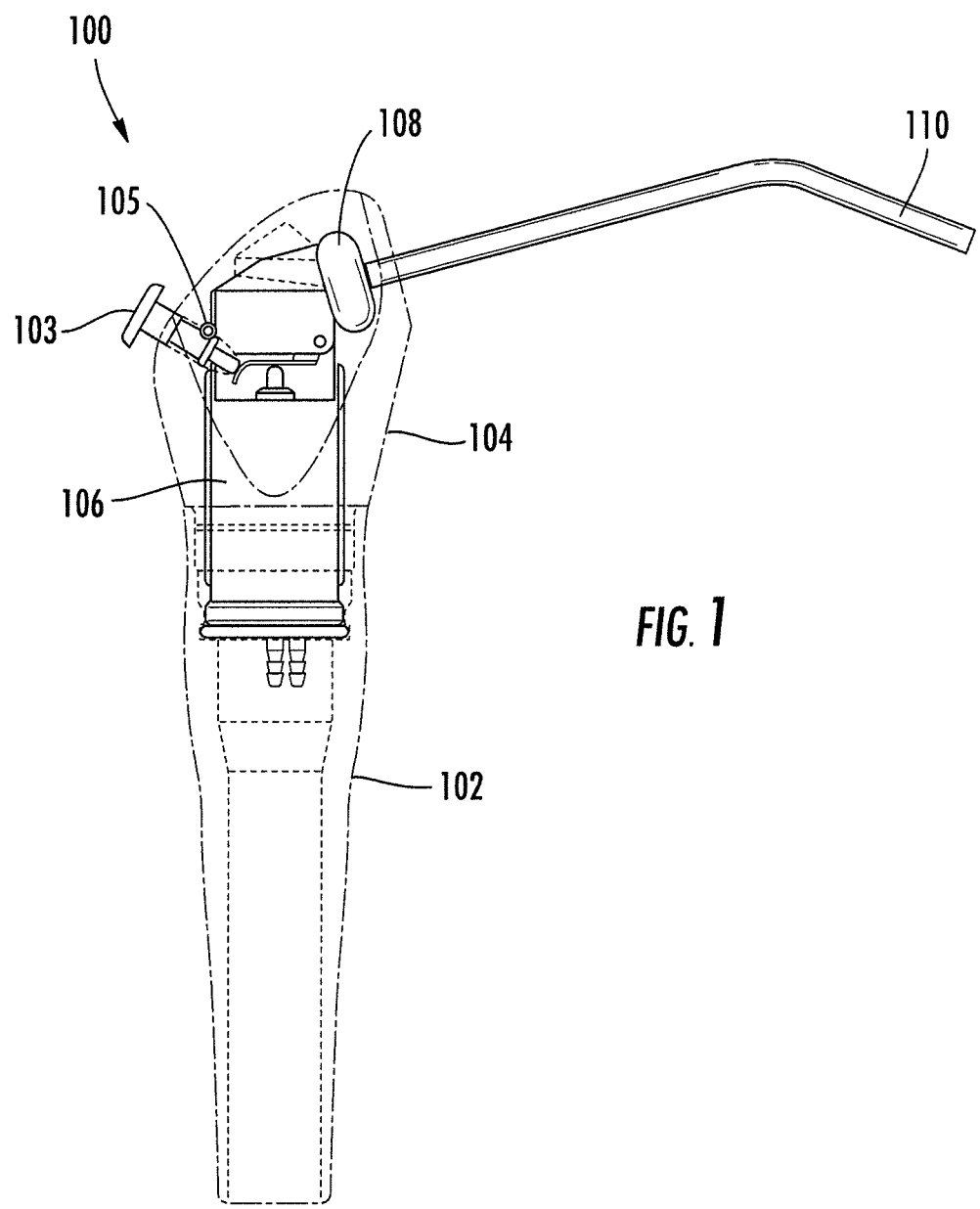
FIG. 1 illustrates a partially transparent side view of an embodiment of a dental syringe.

FIG. 1 illustrates an embodiment of a dental syringe 100. The dental syringe 100 may also be referred to as a 3-way syringe because the dental syringe may be configured to provide a flow of a first fluid, a second fluid, or a combination thereof, such as air, water, or a mist of both air and water. Other fluids may also be dispensed by the dental syringe 100. The dental syringe 100 may generally comprise a handle portion 102 and a head portion 104, which join together. The connection between the head portion and handle portion may occur through a variety of known means including threaded connections and frictional relationships such as through use of one or more o-rings, as may be apparent to one of ordinary skill in the art. The head portion may include one or more buttons 103 and a button retaining pin 105. The dental syringe 100 may further comprise a replaceable valve cartridge 106 and a replaceable tip retention insert 108 for retaining a dental syringe tip 110.

Figure 1A:
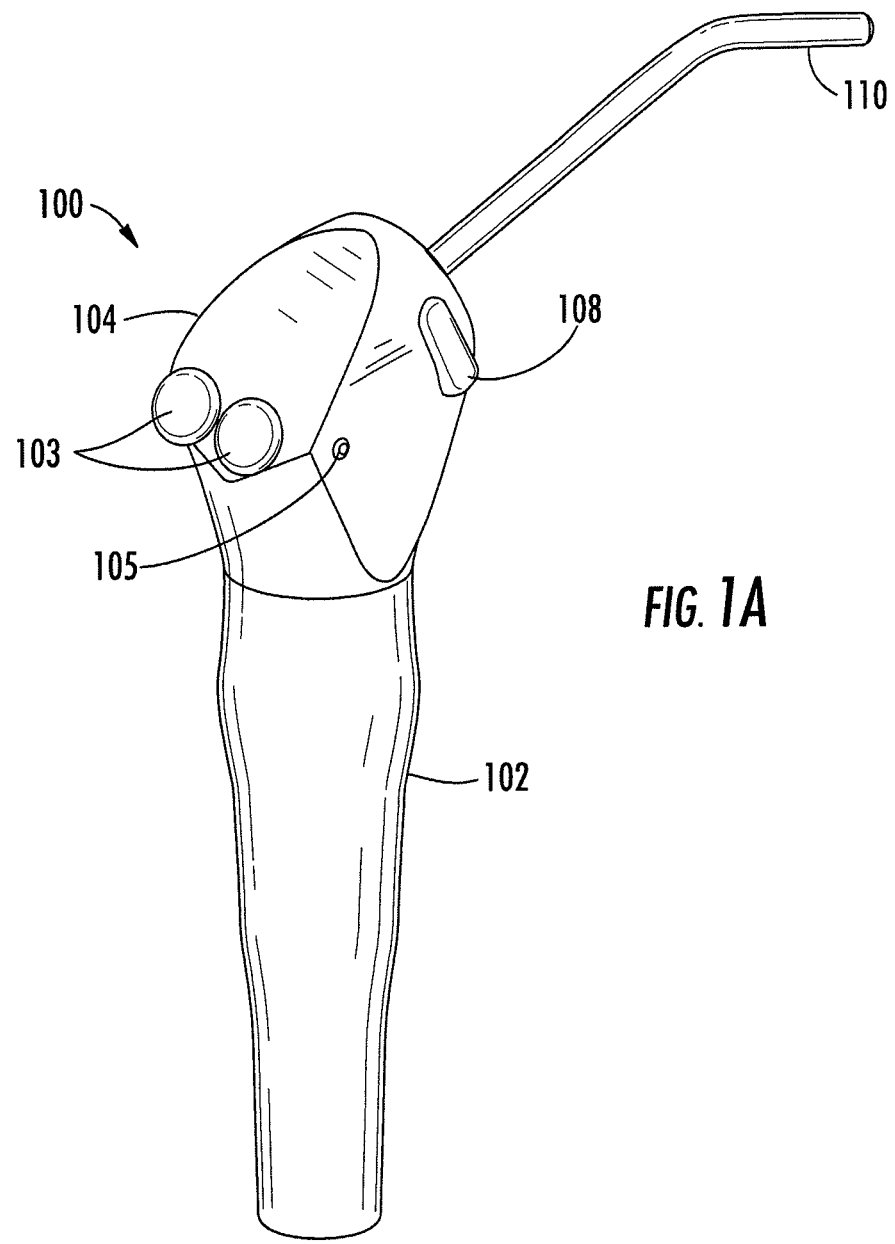
FIG. 1A illustrates a perspective view of the dental syringe of FIG. 1 showing back and side portions.

FIG. 1A illustrates the embodiment of the dental syringe of FIG. 1 from a perspective showing a side, top, and rear of the dental syringe 100. This embodiment shows the handle portion 102 with the attached head portion 104. The head portion comprises a pair of buttons 103 held in by a button retaining pin 105. As may be apparent to one having ordinary skill in the art, the buttons could be held in place by a single pin, a plurality of pins, or one or more other similar devices which prevent the buttons from falling out. The head portion further includes a replaceable tip retention insert 108 for retaining a dental syringe tip 110.

Figure 1B:
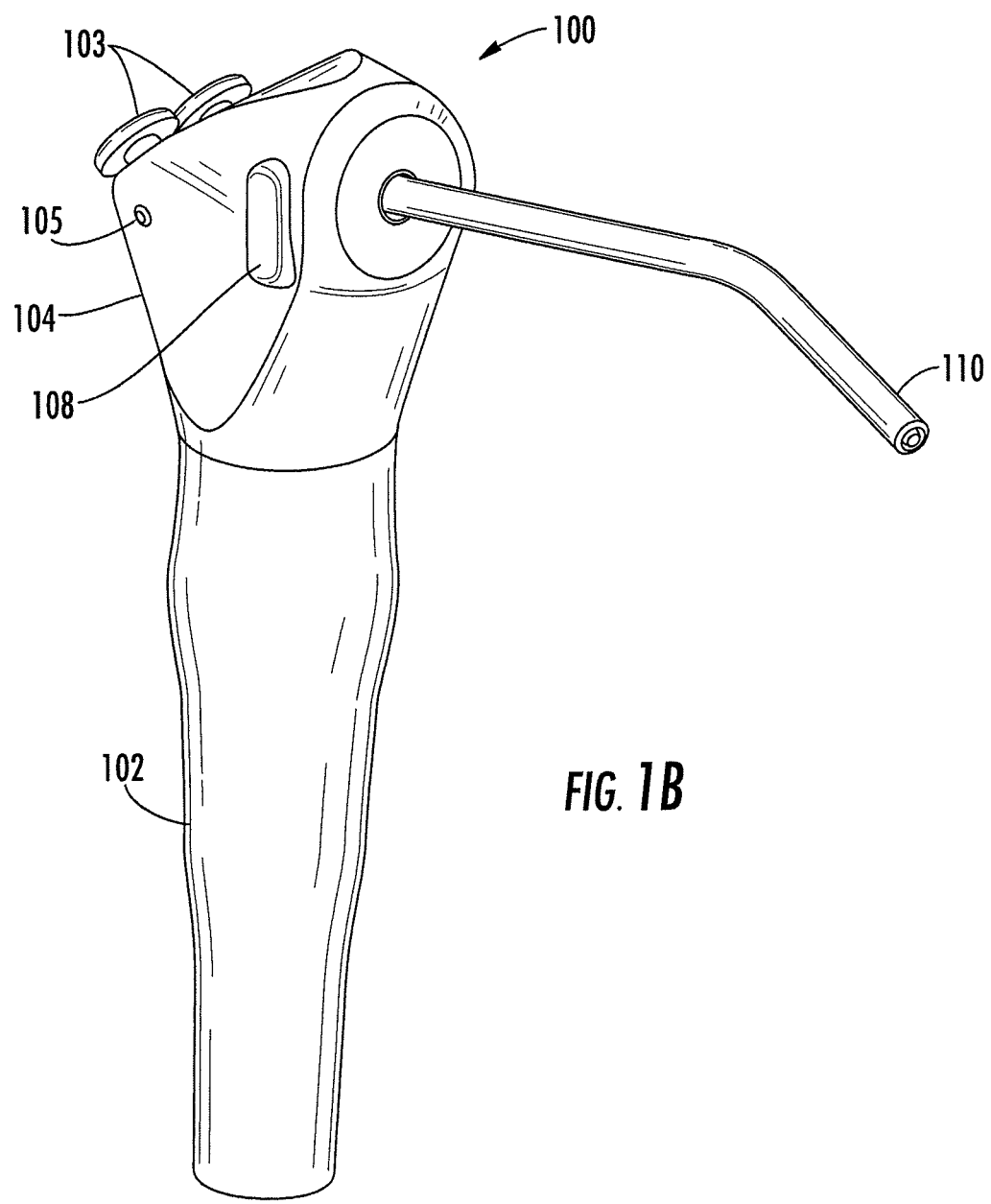
FIG. 1B illustrates a perspective view of the dental syringe of FIG. 1 showing front and side portions.

FIG. 1B illustrates the embodiment of the dental syringe of FIG. 1 from a perspective showing the side and front of the dental syringe 100. This embodiment includes a handle portion 102 with an attached head portion 104. The head portion comprises one or more buttons 103 held in by a button retaining pin 105. The head portion further includes a replaceable tip retention insert 108 for retaining a dental syringe tip 110.

FIG. 2 illustrates a cross-sectional view of a replaceable valve cartridge 206 comprising a flow regulating valve 212. The flow regulating valve 212 is designed to regulate the flow of a fluid which in various embodiments may be, for example, water or air. The flow regulating valve 212, as shown in greater detail in FIG. 2F, may comprise a body 214 which in this embodiment is a plug inserted into the housing 216 of the replaceable valve cartridge 206 and held in place by a plug retaining ring 232, as, for example, by a frictional force. The body 214 defines a flow passageway 218. A piston 220 extends through the flow passageway 218 along an axis 222 corresponding to the lengthwise direction of movement of the piston passing through the flow passageway. A spring 224 is configured to apply a spring force on the piston 220 in a first direction along the axis 222 tending to push the piston in the direction of fluid flow through the flow passageway 218, which in FIG. 2 is an upward direction. By application of the spring force, an opposing seating surface 226 defined by the piston 220 is forced into sealing relation with a seating surface 228 of the body 214, which in FIG. 2 is a sloped surface defined by the body. Because the sloped surface of seating surface 228 is an open end of body 214 having a cylindrical shape, the sloped surface of the seating surface may define an oval shape. A seating seal 230 may aid in the creation of the sealing relationship by compressing when seating surface 228 and the opposing seating surface 226 are relatively more rigid. Such a seating seal 230 may comprise an elastic ring such as a conventional o-ring, and may be optional in embodiments in which one or both of the seating surface 228 or the opposing seating surface 226 have elastic properties, as described more fully below. A piston sealing ring 234 may also create a seal between the body 214 and the piston 220 at a position beyond an outlet 236 from the flow regulating valve 212, at an end of the flow passageway 218 opposite to an inlet defined by the seating surface 228.

As described above, the spring 224 provides a spring force which acts to maintain a seal between the body 214, such as the sloped surface of seating surface 228, and the opposing seating surface 226, which may be facilitated through use of a seating seal 230. It is of note that the seating seal 230 is not shown compressed in all of the figures to more clearly illustrate the interface between the opposing seating surface 226 and the seating surface 228. Also, in alternate embodiments, rather than using or only using a seating seal 230, one or both of the opposing seating surface 226 and the seating surface 228 may be formed with or comprise an elastic material such as various types of rubber, and thus, either the seating surface may be relatively more elastic than the opposing seating surface or, in additional alternate embodiments, the opposing seating surface may be relatively more elastic than the seating surface. Such relationships enable the more rigid of the two surfaces to compress the more elastic of the two surfaces such that a sealing relationship exists. For example, a steel piston may compress a rubber body. Thus, in operation, a first pressurized fluid provided by a first fluid connection 238 will be sealed against traveling through the flow passageway 218 when the flow regulating valve 212 remains in a closed position, as shown in FIG. 2. However, the spring force may be overcome by opposing forces which displace the piston 220 along the axis 222 in a direction substantially opposite to the direction of the spring force. The opposing forces may be provided by a lever mechanism 240 which hinges at a hinge point 242. Accordingly, the application of opposing forces substantially opposite to the force provided by the spring 224 may enable flow through the flow regulating valve 212, as more fully described below.

In accordance with the above description, the selection of the spring will depend on creating the desired balance between the ability of the spring to seal the flow regulating valve properly and the force required to open the flow regulating valve. With further regard to the spring, although various embodiments are shown and described with the spring being positioned below the piston, the spring could alternatively be placed on top of the piston such as in the area between the lever mechanism 240 and the piston sealing ring 234 or in the area between the seating surface 228 and the piston sealing ring. The import consideration in this regard is that the spring must bias the seating surface 228 against the opposing seating surface 226.

In an alternative embodiment, the valve may unseat in a direction opposite to the flow of the fluid. In such an embodiment, a relatively stronger spring would be required, since the spring would have to work against the fluid pressure. However, in such an embodiment the force required to control the flow regulating valve might be more easily modulated by the user.

The operation of an embodiment of a flow regulating valve 212 will now be described in detail with respect to FIGS. 2A-C. As shown in FIG. 2A, the piston 220 is initially biased by a spring force 244 such that the seating surface 228 is in sealing relation with the opposing seating surface 226. Thus, no flow of fluid is able to travel through the flow passageway 218. However, as shown in FIG. 2B, when a first opposing force 246 is applied to the piston 220 in a direction substantially opposite to that of the spring force 244, a small gap 248 may be created at a location on the perimeter of the piston 220 where the spacing is the greatest between the seating surface 228 and the opposing seating surface 226 which allows for a small fluid flow to travel between the seating surface and the opposing seating surface. Thereafter, the flow travels through the flow passageway 218 and then out through an outlet 236.

Further, as shown in FIG. 2C, when a second opposing force 250, which is larger than the first opposing force 246 (see FIG. 2B), is applied to the piston 220, in the same direction substantially opposite to that of the spring force 244, the sealing relationship between the seating surface 228 and the opposing seating surface 226 may be completely removed. In such a situation, a large gap 252 is created between the seating surface 228 and the opposing seating surface 226 such that a large fluid flow may travel through the flow passageway 218 and out the opening 236. Thus, the desired amount of fluid flow through the flow passageway 218 may be achieved by selecting the force applied to the piston 220 and against the spring force 244.

One feature in particular enables regulating the flow of fluid. This feature is that of the angle defined between the seating surface 228 and the opposing seating surface 226. As a result of this angle being defined between the seating surface 228 and the opposing seating surface 226, a gap (see, e.g. 248, 252) defined between the seating surface and the opposing seating surface will not be uniform around the perimeter of the piston 220 as the seating surface and the opposing seating surface unseat. Therefore, a small gap may be created at locations around the perimeter of the piston 220 where the spacing is the greatest between the seating surface 228 and the opposing seating surface 226 which allows for a small flow of fluid therebetween. However, as additional force is applied to the piston 220, the gap may be widened between the seating surface 228 and the opposing seating surface 226 eventually to the extent that the gap extends around the entire perimeter of the piston to allow a larger flow of fluid to enter the flow passageway 218. Accordingly, the flow of fluid between the seating surface 228 and the opposing seating surface 226 may be regulated according to how much flow of fluid is desired by selecting the amount of opposite force applied to the piston.

Although FIGS. 2A-C show a sloped seating surface 228 defined by the body 214 and an opposing seating surface 226 defined by the piston 220, various other alternative embodiments are available. For example, FIG. 2D illustrates an embodiment of a flow regulating valve 212 wherein a sloped seating surface 228' is defined on the piston 220. In this embodiment, the body 214 may comprise a substantially flat opposing seating surface 226'. Further as shown in FIG. 2E, in some embodiments the flow regulating valve 212 may include a first sloped surface of seating surface 228" and additionally the opposing seating surface 226" may comprise a second sloped surface.

In embodiments using two sloped surfaces, the piston may be keyed to prevent it from rotating. For example, the piston may comprise an indexing protrusion, which engages a corresponding portion of the body of the flow regulating valve. The prevention of rotation keeps the valve in a position that maintains the graduated opening function of the valve.

However, in alternate embodiments, the body and/or the piston may be keyed such that the piston can be rotated between a variety of positions. This enables a user to change the relative difference in the angle between the first sloped surface and the second sloped surface. For instance, if the first sloped surface and the second sloped surface are both of equal angles, then at one position, the two surfaces may come together without any relative angular difference between the two surfaces. However, when the piston or body is rotated to a different position, there is an angular difference between the two surfaces. The indexing could provide set positions, such as where there is no relative angular difference between the first and second sloped surfaces and a 180 degree relative rotation of the piston from that position, to make the valve convertible between a regular valve and a flow regulating valve.

Regardless of the particular embodiment and what part or parts of the flow regulating valve comprise a sloped surface or the direction of the sloped surface, an important characteristic, in addition to the durometer of the sealing surface(s), is the relative angle between the seating surface and the opposing seating surface. In some embodiments, the angle defined between the seating surface and the opposing seating surface, may be between 0 and 20°. In particular, in some embodiments the angle may be 10°. The angle is of importance, because the angle enables the partial opening of the flow regulating valve. This is in contrast to many known valves, such as Schrader valves, which open substantially around the entire perimeter of the valve in a non-graduated manner using two parallel planar surfaces. Accordingly, with such known valves, precise control of the amount of flow traveling through the valve is more difficult than with an embodiment of the present flow regulating valve of the present invention.

Alternative embodiments of flow regulating valves are also provided, which may or not be provided in a replaceable valve cartridge. FIG. 2G illustrates a flow regulating valve 2120 designed to regulate the flow of a fluid which may be, for example, water or air. The flow regulating valve 2120 comprises a body 2140 which in this embodiment comprises a head 104 of a dental syringe 100 (see, e.g. FIG. 1A). The body 2140 defines a cavity 2170, a portion of which defines a flow passageway 2180, through which the fluid may flow when the flow regulating valve 2120 is open.

As illustrated in FIG. 2H, a piston 2200, which may be integral with a button 1030, extends through the cavity 2170 along an axis 2220 having first (e.g. outward) and second (e.g. inward) directions, upon which the piston axially moves. The piston 2200 may extend through one or more centering sleeves such as first, second, and third centering sleeves 2205, 2206, 2207 which allow axial movement of the piston, but substantially restrict other movement. The piston 2200 may also extend through a number of seals, such as a flow-control seal 2230, a flow passageway end seal 2232, and a second flow passageway end seal 2234. The flow passageway 2180 is defined between the flow passageway end seal 2232 and the second flow passageway seal 2234. The flow passageway end seal 2232 may be positioned in the second direction from the flow-control seal 2230, and the second passageway end seal 2234 may be positioned in the first direction from the flow-control seal 2240. The sleeves 2205, 2206, 2207 and seals 2230, 2232, 2234 may be retained in the cavity 2170 by a first retaining member which may comprise a retaining pin 2105. The retaining pin 2105 extends at least partially through the body 2140 and restrains movement of the seals 2230, 2232, 2234 and sleeves 2205, 2206, 2207 in the first direction along the axis 2220 which is generally outward as illustrated in FIG. 2H. In the illustrated embodiment this is accomplished by positioning the retaining pin 2105 such that the third centering sleeve 2207 contacts the retaining pin 2105. Thus, the first centering sleeve 2205, the second centering sleeve 2206, and the seals 2230, 2232, 2234 may be prevented from moving in the first direction by at least indirectly contacting the retaining pin 2105.

A spring 2240 positioned within a cavity 2210, or other force means, is configured to apply a force on the piston 2200 in the first direction along the axis 2220 tending to push the piston outward. Other embodiments of force means may include a fluid source, such as pressurized air, configured to supply a fluid force to the piston 2200. The fluid source may be supplied to the cavity 2210. In an alternate embodiment opposing magnetic polarities may be applied to the piston and one or more objects displaced inwardly from the piston in the second direction or the body itself. Other force means may be used so long as they are configured to supply a force on the piston 2200 in the first direction along the axis 2220 tending to push the piston outward. The spring 2240 and cavity 2210 (or other force means) may be positioned coaxially with the piston 2200 and the cavity may thus comprise a portion of the cavity 2170. A second retaining member may couple to the piston 2200 in the cavity 2210. The second retaining member may comprise an e-clip or c-clip which snaps into a clip groove 2250 (see FIG. 2K") defined in a portion of the piston 2200 which may positioned in the cavity 2210. In an alternate embodiment, the second retaining member comprises a nut 2107. When compressed, the spring 2240 applies a force to the nut 2107 in the first direction, but the movement of the nut and piston 2200 is at least partially restrained by indirect contact between the nut and the retaining pin 2105. In particular, the nut 2107 may contact a spacer 2109 which may in turn indirectly contact the retaining pin 2105 through the seals 2230, 2232, 2234 and sleeves 2205, 2206, 2207 to restrain movement of the piston 2200 in the first direction. When the second retaining member comprises an e-clip or c-clip, the second retaining member may still operate in substantially the same way.

Regarding operation of the flow regulating valve 2120, when the button 1030 is depressed, the piston 2200 moves in the second direction along the axis 2220 which is opposite to the first direction, and thus generally inward as viewed in FIG. 2H. The seals 2230, 2232, 2234 and sleeves 2205, 2206, 2207, however, are substantially restrained from movement in the second direction by a lip 2111 defined at the entrance to the cavity 2210, which may be created by forming the cavity of a smaller diameter than the cavity 2170. Thus, when the button 1030 is depressed, the piston 2200 moves relative to the seals 2230, 2232, 2234 and sleeves 2205, 2206, 2207.

This movement controls the flow of fluid through the flow control valve 2120. FIG. 2I illustrates a modified perspective view of the flow control valve 2120 to show the flow path to and through the flow control valve. Fluid is supplied to the flow control valve 2120 by a fluid supply conduit 2380 which includes a supply slot 2380' which is in fluid communication with a first portion 2181 of the flow passageway 2180 defined between the flow-control seal 2230 and the flow passageway end seal 2232. The fluid supply conduit 2380 may be configured to provide a fluid flow applied at the perimeter of the piston 2200. Further, the fluid supply conduit 2380 may in some embodiments be oriented such that the pressurized fluid is directed at the piston 2200 substantially perpendicularly to the axis of the 2220. Substantially perpendicular herein means any configuration wherein the fluid supply conduit 2380 directs the fluid such that is five or more degrees away from parallel with the axis 2220. Providing a fluid flow applied at the perimeter of the piston 2200 in the first portion 2181 of the flow passageway 2180 may prevent fluid pressure from producing a force on the piston in the first direction such as where a fluid supply is provided from below the piston axis within the cavity 2210. Such a force may be undesirable because it increases the necessary force in the second direction that the user must produce to actuate the flow control valve 2120. In particular, the user may have to overcome the force produced by the spring 2240 as it is compressed during actuation of the flow control valve 2120. Therefore, any additional force in the first direction may make the flow control valve 2120 more difficult to actuate.

In addition to providing flow applied at the perimeter of the piston 2200, the flow control valve 2120 may comprise additional features intended to substantially prevent the production of fluid force in the first direction. Returning to FIG. 2G, one such feature is that the cavity 2210 may be in communication with a cavity pressure, such as ambient air pressure, wherein cavity pressure is less than the pressure in the fluid supply conduit 2380. By allowing the cavity 2210 to communicate with ambient air pressure, the force applied to the piston 2200 in the second direction will not have to overcome force produced by compression of fluid within the cavity as the piston moves in the second direction. Some embodiments of flow control valves 2120 may include a pressure relief conduit 2382, which may comprise a passage in the body 2140 leading from the cavity 2210 to the outside of the body to facilitate communication with ambient air pressure.

Certain embodiments of flow control valves 2120 may additionally or alternatively be configured such that the fluid supply conduit 2380 is out of fluid communication with the distal ends 2200a, b (see FIG. 2H) of the piston 2200. By keeping the distal ends 2200a, b of the piston 2200 out of fluid communication with the fluid supply conduit 2380, the force on the piston in the second direction required to operate the flow control valve 2120 may not have to overcome force created by the pressurized fluid in the fluid supply conduit. To prevent the fluid supply conduit 2380 from communicating with the cavity 2210, and hence the distal end 2200b of the piston 2200, the flow passageway end seal 2232 may be sized and positioned such that it contacts the piston 2200 and the body 2140 to thereby separate the first portion 2181 of the flow passageway 2180 from the cavity. Additionally or alternatively, the flow control valve 2120 may be configured such that the total area of the piston 2200 perpendicular to the axis 2220 which is exposed to force from pressurized fluid in the second direction is greater than the total area of the piston perpendicular to the axis which is exposed to force from pressurized fluid in the first direction. This may present an alternate way to prevent pressurized fluid in the fluid supply conduit 2380 from producing a net force in the first direction which a user would have to overcome when pressing on the button 1030 to operate the flow control valve 2120. In alternate embodiments the total area of the piston 2200 perpendicular to the axis 2220 which is exposed to force from pressurized fluid in the second direction may be equal to, or less, than the total area of the piston perpendicular to the axis which is exposed to force from pressurized fluid in the first direction. These alternate embodiments would produce substantially no net force and a force in the second direction, which may be desirable in some embodiments.

Returning to description of the operation of the flow control valve 2120, when the flow control valve is closed, as illustrated in FIG. 2I, the fluid is at least substantially prevented from flowing from the first portion 2181 to a second portion 2182 of the flow passageway 2180, which may be defined between the flow-control seal 2230 and the second flow passageway end seal 2234. In particular, flow control seal 2230 contacts both the body 2140 and the piston 2200 to prevent flow between the first portion 2181 and the second portion 2182 of the flow passageway 2180. However, when the button 1030 is pressed, the piston 2200 translates along the axis 2220 in the second direction (inwardly as illustrated in FIG. 2I), such that the flow control valve 2120 opens. As illustrated in FIG. 2J, a flow path is thereby created through the flow control valve 2120, which puts the fluid supply conduit 2380 in fluid communication with a fluid outlet slot 2381', which is part of a fluid outlet conduit 2381, which may supply the fluid to a syringe tip 110 (see, e.g. FIG. 1A) positioned within a syringe tip cavity 2160. The fluid travels from the fluid supply conduit 2380 through the first portion 2181 of the flow passageway 2180, through the second portion 2182 of the flow passageway, and then through the outlet conduit 2381 (see FIG. 2J). The flow may be at least partially directed from the second portion 2182 of the flow passageway 2180 to the outlet conduit 2381 by the second flow passageway end seal 2234, which may substantially prevent the fluid from traveling out of the cavity 2170 in the first direction near the button 1030.

The flow path through the flow passageway 2180 may be more clearly seen in FIG. 2K. When the piston 2200 moves inwardly as a result of the user pushing down on the button 1030 in the second direction (see FIG. 2J) the flow-control seal 2230 may come at least partially out of contact with the piston at a flow-control groove 2330, or other flow-control means may otherwise allow fluid communication between the first portion 2181 and the second portion 2182 of the flow passageway 2180. This occurs, for example, when the flow-control groove 2330 extends at least partially beyond the flow-control seal 2230 in both the first and second directions. Thereby a flow path is created such that fluid may flow from the first portion 2181 of the flow passageway 2180 to the second portion 2182 of the flow passageway by traveling between the flow-control seal 2230 and the piston 2200 within the flow-control groove 2330. When the user releases the button 1030, the piston 2200 moves in the first direction as a result of the force from the compressed spring 2240, which thereby moves the piston back into sealing contact with the flow-control seal 2230 as the flow-control groove 2330 is displaced from the flow-control seal in the first direction. When a second centering sleeve 2206 is used, the fluid will flow through an inlet aperture 2206*a* in the second centering sleeve to reach the flow control groove 2330 from the fluid supply conduit 2380 (see FIG. 2J). Thereafter, in embodiments comprising a first centering sleeve 2205, the fluid will flow from the flow-control groove 2330 through an outlet aperture 2205*a* in the first centering sleeve to reach the fluid outlet conduit 2381 (see FIG. 2K').

Thus, the flow of fluid through the flow control valve 2120 may be allowed or prevented by controlling the position of the piston 2200. However, in some embodiments the flow-control valve 2120 may include features configured to facilitate control of the flow-rate through the valve. To accomplish this, embodiments of the flow-control groove 2330 may comprise a shape such that at least a portion of the piston 2200 at the flow-control groove defines a plurality of cross-sections perpendicular to the axis 2220 of the piston which generally decrease in area from the farthest portion of the flow-control groove in the second direction towards the first direction until a maximum groove depth is reached. In such configurations, the flow-control seal 2230 may break the seal with the piston 2200 gradually as the piston is displaced in the second direction. Thus, one or more small gaps may be created between the piston 2200 and the flow-control seal 2230 at the one or more flow-control grooves 2330 as the piston is initially displaced in the second direction. Due to the decreasing cross-sectional area of the piston 2200 at the flow-control seal 2230, as the piston is further displaced in the second direction, the one or more gaps between the flow-control seal and the piston increase in size or number. Thus, a larger quantity of fluid may flow through the flow control valve 2120 as the piston 2200 is displaced further in the second direction. Accordingly, a user may selectively control the flow through the flow control valve 2120 by changing the position of the flow-control groove 2330 relative to the flow-control seal 2230 by moving the piston 2200.

Other flow-control means may be used including other embodiments of flow-control grooves that are structural with an alternate shape and/or cross-section linearly along axis 2220 or radially around piston 2200. Also, a flow-control groove may be shaped without a specific intent to assist the control of the flow-rate, such as if the flow-control groove is a uniform reduced diameter section of the piston 2200. In certain other embodiments the flow-control means may comprise a bore through the piston 2200, the bore comprising at least first and second apertures which are displaced along the axis 2220. Regardless of the particular embodiment of the flow-control means, it will be configured such that the first portion 2181 of the flow passageway 2180 is not in fluid communication with the second portion 2182 of the flow passageway when the piston 2200 is in the first position, but is in fluid communication with the second portion of the flow passageway when the piston is in the second position. The various embodiments of flow-control means may or may not have characteristics intended to assist in controlling the fluid flow-rate. For example, the flow-control means may be configured to permit increasing flow of fluid through the valve as the piston is displaced in the second direction.

FIGS. 2K"-2K"" illustrate one embodiment of a piston 2200 with flow-control grooves 2330. As illustrated, the piston 2200 may comprise a plurality of flow control grooves 2330. As discussed above, the flow rate through the valve may be adjusted in a number of ways. In particular, the number of flow-control grooves 2330 may be changed. The piston 2200 may comprise various numbers of flow-control grooves 2330, such as 2, 4, or 6, although other numbers of flow-control grooves may be used. As may be seen in FIG. 2K''', which is an enlarged portion of the cross-section of the piston 2200 from FIG. 2K", each flow-control groove 2330 may taper in depth, as described above. Each flow control groove 2330 may taper in depth along a length 2252 and/or across a width 2254 as respectively illustrated in FIGS. 2K'''' and 2K'''''. Such features may adjusted to control the flow rate through the flow control valve 2120.

Flow control may additionally or alternatively be accomplished by using a metering screw 3000, which may comprise a portion of the fluid supply conduit 2380 as illustrated in FIG. 2L. In particular, the metering screw 3000 may be positioned within a body 2140 such as a head portion 3104 of a dental syringe. However, the metering screw may be used in various other positions and embodiments wherein it may be desirable to control the flow of a fluid. It should be noted that the metering screw 3000 and the flow control valve 2120 affect flow in different ways, and hence they may be used in combination. In this regard, the metering screw 3000 generally controls the maximum fluid flow rate through a dental syringe. In comparison, the flow control valve 2120 controls the real-time metering of fluid out of the tip of the dental syringe, up to the maximum flow rate as defined by the metering screw. Thus, the flow control valve 2120 and metering screw may work in conjunction to provide the desired operation of the dental syringe.

As illustrated in FIG. 2L, the metering screw 3000 may comprise a cylindrical end portion 3002 having a first diameter which is configured to be received by a metering cavity 3012 in the body 2140. The metering cavity 3012 comprises a cylindrical end cavity 3012a having a second diameter which is greater than the first diameter defined by the cylindrical end portion 3002. The cylindrical end portion 3002 is moveable from an extended position (FIG. 2L) to a retracted position (FIG. 2N). When the cylindrical end portion 3002 is in the extended position, the metering screw 3000 occupies a first volume of the metering cavity 3012, and when the cylindrical end portion is in the retracted position, the metering screw occupies a second volume of the metering cavity, wherein the second volume is less than the first volume. Thus, when the metering screw 3000 is in the extended position, a relatively small flow 3100 is allowed to travel around the metering screw through the fluid supply conduit 2380 (FIG. 2L), whereas when the metering screw is in the retracted position, a relatively large flow 3100' is allowed to travel around and past the metering screw (FIG. 2N).

The metering screw 3000 may comprise a threaded portion 3004 configured to screw into a threaded receiving portion 3006 of the metering cavity 3012. The metering screw 3000 may further comprise a cutout portion 3008 configured to receive the tip of a screwdriver or a similar tool. Thus, by inserting the tip of a screwdriver, for example, in the cutout portion 3008, the metering screw 3000 may be rotated to retract or extend the metering screw. In so doing, the movement of the threaded portion 3004 of the metering screw 3000 with respect to the threaded receiving portion 3006 of the metering cavity 3012 causes axial translation of the metering screw such that it retracts from or extends into the metering cavity 3012. In alternate embodiments, the metering screw may comprise a handle, lever, or other device which may allow the metering screw to be adjusted without requiring a separate tool. Regardless of the particular adjustment mechanism used, leakage of fluid out of the metering cavity 3012 between the threaded portion 3004 of the metering screw 3000 and the threaded receiving portion 3006 of the metering cavity may be prevented by a seal 3020, which may comprise an o-ring seal. The seal 3020 may contact both the metering screw 3000 and the metering cavity 3012 to thereby prevent flow out of the metering cavity past the threaded portion 3004 of the metering screw.

The metering screw 3000 may be configured such that the fluid supply conduit 2380 is in fluid communication with the first portion of the flow passageway 2181 (see FIG. 2J) regardless of whether the cylindrical end portion 3002 is in the extended position (FIG. 2L) or the retracted position (FIG. 2N). This is due to the first diameter of the cylindrical end portion 3002 being less than the second diameter of the cylindrical end cavity 3012a as described above. As a result of the difference in diameters, in the extended position a relatively small fluid flow 3100 may pass by the metering screw by flowing around the cylindrical end portion 3002 of the metering screw 3000 in the gap between the first diameter and the second diameter.

Because in some embodiments both the head portion 3104 of a dental syringe and the metering screw 3000 may be formed from metal or other incompressible materials, the head portion and the metering screw may not form a perfect seal against one another. Therefore, an alternate embodiment of a metering screw 3000' and corresponding fluid flow metering system are also provided. As illustrated in FIGS. 2M and 2O, a cylindrical end portion 3002' of the metering screw 3000' may comprise a compressible material, which may be elastomeric, such that when the metering screw is extended into the cavity 3012, the cylindrical end portion 3002' may be compressed along the longitudinal axis of the metering screw, which may cause a radial expansion of the cylindrical end portion such that it would cause the cylindrical end portion to substantially entirely seal against the metering cavity 3012, so that flow is substantially entirely blocked. Further, as a result of forming the cylindrical end portion 3002' from a compressible material, use of an o-ring (e.g. o-seal 3020) may not be required because the cylindrical end may be dimensioned such that it sealingly contacts the body 2140 and thereby substantially prevents flow of fluid out of the metering cavity 3012 past a threaded portion 3004' of the metering screw. Similarly to the previously discussed embodiments, the metering screw 3002' may be moved to a retracted position wherein the compressible cylindrical end portion 3002' of the metering screw 3000' is at least partially out of contact with the cylindrical end portion to allow flow of the fluid therethrough.

The metering screw 3000' may include a threaded portion 3004' defining a first end rotatably operable by a user such as through use of the cutout portion 3008' defined in the first end. The threaded portion 3004' may also define a second end defining a cavity 3004a' which receives the compressible cylindrical end portion 3002' which extends therefrom along an axis. The cylindrical end portion 3002' may include a spherical end 3002a' which is configured to engage a corresponding spherical end 3011' of the metering cavity 3012. In some embodiments, the threaded portion 3004' of the metering screw 3000' may be formed from a different material than the cylindrical end portion 3002' of the metering screw. For example, the threaded portion 3004' may be formed from a metal or other substantially rigid material which facilitates use of the cutout portion 3008' when adjusting the metering screw 3000' by screwing it in or out.

Returning to the replaceable valve cartridge, FIG. 3 illustrates an embodiment of a replaceable valve cartridge 306 separate from corresponding head and handle portions of a dental syringe. The replaceable valve cartridge 306 may comprise a housing 356 having one or more indexing protrusions 358. As shown in FIG. 3A, the indexing protrusions 358 may engage corresponding indentions 360 in the head portion 304 of a dental syringe 100. As previously described, the replaceable valve cartridge 306 may include one or more flow-regulating valves 212, which may be substantially enclosed within the housing 356. Accordingly, FIGS. 3 and 3A-3C illustrate embodiments of a replaceable valve cartridge 306 configured to include one or more pistons 320 extending from the housing 356. These pistons 320 may be engaged by levers 340 to operate the flow regulating valves 212.

With reference to FIG. 3A, one or more buttons 303 are movably operable to engage the levers 340 to actuate the pistons 320 and thereby operate the valves 212. Referring to FIG. 3B, the housing 356 may comprise three cavities 362', 362", and 362'". Each cavity 362', 362", and 362'" may house a corresponding valve mechanism. For example, a first cavity 362' may house a flow regulating valve 212 controlling the flow of air through the replaceable valve cartridge 306. Also, a second cavity 362" may house a flow regulating valve 212 controlling the flow of water through the replaceable valve cartridge 306. The third cavity 362'" in the housing 356 of the replaceable valve cartridge 306 may house a system to remove a residual liquid from a tip of the dental syringe, as will be described in detail below.

Referring to FIG. 3A, it was previously noted that the indexing protrusions 358 align the replaceable valve cartridge 306 with the head portion 304 of a dental syringe. Further, as shown in FIGS. 3 and 3A, the replaceable valve cartridge 306 may comprise a seating shoulder portion 364 which engages a corresponding inside surface of the head portion 304 of a dental syringe when the replaceable valve cartridge is fully inserted within the head portion. Accordingly, proper alignment and insertion depth of the replaceable valve cartridge 306 within the head portion 304 may be achieved with relative ease. Referring now to FIG. 3C, the replaceable valve cartridge 306 may further comprise a seal 366 for sealing an axially inserted dental syringe tip. The seal 366 for sealing an axially inserted dental syringe tip, which will be described in greater detail below, may allow fluid which escapes past the seal to be in communication with a bleed path 368 (see FIG. 3B) out of the housing 356 of the replaceable valve cartridge 306. Once the fluid escapes out of the bleed path 368, the fluid could potentially fill the head portion 304 (see FIG. 3A). To avoid this, and to allow the user of the dental syringe to know when the seal 366 is leaking, the replaceable valve cartridge may further include a notch 369, which allows the fluid escaping past the seal and through the bleed path 368 to travel through the notch and out of the bottom of the dental syringe. Thus, the user of the dental syringe may be able recognize that the seal 366 is not working properly.

With regard to the positioning of the levers 340, as shown in FIG. 3C, each may be positioned on opposing sides of the seal 366 for sealing an axially inserted dental syringe tip. Further, when the replaceable valve cartridge 306 is inserted into the head portion 304 of the dental syringe, the seal 366 for sealing an axially inserted dental syringe tip may be configured to align with an aperture 370 (see FIG. 3A) in the head portion. Such a configuration allows for axial insertion of a dental syringe tip along a longitudinal axis of the seal 366 for sealing an axially inserted dental syringe tip.

Returning to the cavities 362', 362", and 362'" in the housing 356 which may house valves, one or more of the cavities may include a fluid connection 372', 372", such as shown in FIG. 3 or FIG. 3A. For example, the first cavity 362' may be in fluid communication with a first connection 372' and the second cavity 362" may be in fluid communication with a second fluid connection 372". Additionally, a third valve mechanism, such as a system to remove a residual liquid from the tip of a dental syringe, may be in fluid communication with the first fluid connection 372', as will be discussed later. In such an embodiment the first fluid may comprise a gas such as air.

Thus, the above described replaceable valve cartridge houses many of the moving parts in a dental syringe in a single replaceable valve cartridge. Accordingly, operation and maintenance of a dental syringe may be substantially simplified, particularly in light of the ability of the dental syringe to separate into a head portion and a handle portion and allow for easy insertion and removal of the replaceable valve cartridge. Thus, a dental assistant may be able to replace the replaceable valve cartridge with relative ease. In comparison, many prior art dental syringes require special tools and expertise to take apart the dental syringes, and hence many prior art dental syringes may not be fully serviceable by dental assistants.

FIGS. 4 and 4A-4I illustrate additional features of embodiments of the dental syringe. The head portion 404 of the dental syringe may comprise a tip retention insert 408 as shown in FIG. 4. As shown in FIG. 4A, the tip retention insert 408 may comprise a housing at least partially defining a cavity 474 configured for insertion of a dental syringe tip. As shown in FIG. 4B, such a cavity 474 may align with an aperture 476 in the head portion 404 of the dental syringe which together enable insertion of a dental syringe tip.

As shown in FIGS. 4A and 4B, the tip retention insert 408 may further comprise one or more releasable cartridge retentioners 478. The releasable cartridge retentioners 478 may be configured to releasably hold the tip retention insert 408 in a head portion 404 of a dental syringe by engaging corresponding cavities 479. The releasable cartridge retentioners 478 may be released by breaking the interference fit formed by the releasable cartridge retentioners and corresponding cavities 479 in the head portion 404, such as through inserting relatively thin and flat objects between the releasable cartridge retentioners and the corresponding cavities. For example, a flat head screw driver having a very thin head may be able to remove the tip retention insert 408. Alternatively, the tip retention insert 408 may be removed in some embodiments by applying sufficient pressure on one side of the tip retention insert to overcome the retention force and push the insert out of the side of the head portion 404. Accordingly, the tip retention insert 408 may be replaceable from the head portion 404 of a dental syringe in certain embodiments.

In general, the tip retention insert 408 may comprise one or more clamping members movably positioned around the cavity 474. As shown in the embodiment of FIG. 4A, the clamping members may comprise a first plate 480' and a second plate 480". Embodiments of the tip retention insert 408 may further generally comprise one or more springs configured to bias the clamping members at least partially into the cavity 474. As shown in the embodiment of FIGS. 4C-4E, the springs can be coil springs 482. The embodiments of the tip retention insert 408 shown in FIGS. 4C-4E further include a plurality of buttons 484 configured to move both plates 480', 480" against the force of the spring 482. In particular, in the illustrated embodiments, each plate 480', 480" is fixed to a corresponding button. As may be apparent to one of ordinary skill in the art, in alternate embodiments, a single button may be configured to move one plate against the force of a spring to release and secure a dental syringe tip. Such a button could alternatively extend from the top of the head portion of the dental syringe instead of a side.

FIG. 4F illustrates an embodiment of the first plate 480' and FIG. 4G illustrates an embodiment of the second plate 480" from FIGS. 4A-4E. As shown in FIG. 4C, when the two buttons 484 are displaced inwardly towards one another, the cavity 474 comprises a relatively large area allowing for axial insertion of a dental syringe tip 410 because the plates 480', 480" slide into such a position that rounded larger open sections 485', 485"of the plates overlap. However, as the buttons 484 are released, the two plates 480', 480" move to such a position that angled locking sections 487', 487" overlap to form a relatively smaller cavity 474, which may lock onto a dental syringe tip 410 to provide a secure interlocking connection, as shown in FIGS. 4D and 4E.

In various embodiments, the tip retention insert 408 may lock onto different shapes of dental syringe tips 410. Depending on the particular dental syringe tip 410 which is being engaged, the plates may take different forms. In particular, when in a locked configuration such as shown in FIGS. 4D and 4E, the angled locking sections 487', 487" of the two plates 480', 480" may combine to form a cavity 474 in the shape of a pentagon or in alternative embodiments the cavity may take the form of a hexagon. For example, when a dental syringe tip is shaped like a hexagon, the angled locking sections of the plates may preferably also form a hexagon so that the angled locking sections may engage all six sides of the dental syringe tip and thereby help to prevent rotation of the dental syringe tip. As will be apparent to one of ordinary skill in the art, various other cavity shapes may be usable depending on the shape of the particular dental syringe tip being inserted into the dental syringe. An important consideration in this regard is the shape of the cavity formed by the angled locking sections of the two plates when they are in the locked position. The shape of the cavity formed by the rounded larger open sections of the two plates when the two plates are in an unlocked position may take many different forms so long as the cavity is large enough to allow for insertion of the dental syringe tip.

FIGS. 4H-4J illustrate an alternate embodiment of a tip retention insert 408'. In this embodiment, the tip retention insert 408' is configured to hold both regular (non-indexing) and indexing syringe tips 410. FIG. 4H illustrates the tip retention insert 408' in an open position which allows for the insertion of a dental syringe tip 410 due to the two buttons 484' being displaced inwardly towards one another, as described in the embodiment of FIGS. 4C-4G. When the buttons 484' are depressed, two rounded larger open sections 483', 483" of two plates 481', 481", which may be substantially similar to one another but oriented in opposite directions, combine to form a large cavity 474' which allows for insertion of the dental syringe tip 410.

FIG. 4I illustrates the embodiment of the tip retention insert 408' of FIG. 4H in which the two buttons 484' have been released and hence the two plates 481', 481" clamp against the dental syringe tip 410, which in this figure comprises a regular (non-indexing tip). Accordingly, intermediate locking sections 489', 489" form a smaller cavity 474' and engage the dental syringe tip 410 in order to hold it in place. The intermediate locking sections 489', 489" may combine to form a radius that is slightly smaller than that of the dental syringe tip 410, such that the dental syringe tip may be securely engaged.

FIG. 4J also illustrates the embodiment of the tip retention insert 408' of FIG. 4H. However, in this embodiment, the tip retention insert 408' is illustrated as locking onto an indexing dental syringe tip 410. In such an embodiment, distal locking sections 491', 491" engage the dental syringe tip 410. The distal locking sections 491', 491" form a cavity 474' with a cross-section that is smaller than the cross-section formed by the intermediate locking sections 489', 489" (see FIG. 4I). Thus, indexing syringe tips 410 having a number of opposing flat sections 493, e.g. 2, 4, 6, 8, etc., may be locked in place by the distal locking sections 491', 491" of the tip retention mechanism 408'. Accordingly, the embodiment of a tip retention insert 408' illustrated in FIGS. 4H-4J may hold both indexing and regular dental syringe tips 410.

FIGS. 4K and 4L illustrate an alternate embodiment of the tip retention insert 408". In this embodiment, the clamping members may comprise a plurality of ball bearings 486 wherein one or more springs provide a radially inwardly directed force on each of the ball bearings. In such an embodiment the spring may comprise a torsion spring 488', 488". Such an embodiment of the tip retention insert 408" may further comprise a plurality of spacer elements 490', 490" positioned between the ball bearings 486 and configured to hold each of the ball bearings in a respective channel 492. As in the case with the previously described embodiments of tip retention inserts, one or more buttons 484" may be used to release a syringe tip 410. In particular, in this embodiment when the one or more buttons 484" are compressed, the radially inwardly directed spring force on the ball bearings 486 is reduced as the diameter of the torsion spring 488', 488" enlarges and hence axial insertion or removal of a dental syringe tip 410 is enabled. This allows for quick and easy dental syringe tip insertion and removal. In comparison, some prior art dental syringes require tools and more cumbersome procedures to replace dental syringe tips.

When one or more buttons 484" are released, the spring tension returns to the ball bearings 486 as the diameter of the torsion spring 488', 488" reduces and hence the ball bearings 486 compress upon the dental syringe tip 410 from various radial directions to hold the dental syringe tip in place. As is the case with previously described embodiments of the tip retention insert, the number and type of clamping members may be selected to prevent rotation of the dental syringe tip. Further, the number and type of clamping members may be selected to provide an indexing function. Indexing and prevention of rotation of the dental syringe tip may be preferable in certain applications because it is known to use a dental syringe tip to engage the inside of a cheek of the mouth and push or pull the cheek during certain oral procedures, and hence a rotationally fixed dental syringe tip is preferable in certain applications.

The cross-section illustrated in FIG. 4K and the modified cross-section illustrated in FIG. 4L show how the spring 488" connects to both of the buttons 484". However, as will be apparent to one of ordinary skill in the art, alternate embodiments may use a spring connecting to a single button. Further, as shown in both of the embodiments of FIGS. 4K and 4L, the buttons 484" may be hingedly connected to the rest of the tip retention insert 408". As will be apparent to one of ordinary skill in the art, various other mechanisms allowing for compression of the spring may be used, such as simple lever mechanisms. Alternatively, two opposing plates could slide inwardly to apply force radially inwardly on the plurality of balls in place of the torsion springs.

Referring now to FIG. 5, a dental syringe may comprise a bleed-over prevention manifold for sealing an axially inserted dental syringe tip, such as included in a replaceable valve cartridge. Embodiments of such a bleed-over prevention manifold may be configured to direct a first fluid through a first fluid path, direct a second fluid through a second fluid path, prevent bleed-over of the first fluid into the second fluid path and prevent bleed-over of the second fluid into the first fluid path, as will be described below. Thus, as shown in FIG. 5, a bleed-over prevention manifold 594 may comprise a first channel 596 defined between a first ring 598 of a first elastic portion and a second ring 5100 of a second elastic portion. As will be described below, the first channel 596 may define a low pressure zone configured to permit any of a first fluid and a second fluid which reaches the first channel to exit through a bleed path. One embodiment of a bleed path is shown in FIG. 5A. In such an embodiment, the bleed path 5102 comprises a hole in the housing 556 of the replaceable valve cartridge 506 in which the bleed-over prevention manifold 594 is inserted.

Referring to FIG. 5, the bleed-over prevention manifold 594 may further comprise a second channel 5104. FIG. 5B illustrates an embodiment of a bleed-over prevention manifold 594 in which the second channel 5104 is in fluid communication with the first channel 596. Such fluid communication can occur through, for example, one or more holes 5106 extending through the bleed-over prevention manifold 594 which link the first channel 596 and second channel 5104. With further regard to the first channel 596, the first channel may be defined by a first outer surface 5108 of the first ring 598 and a second outer surface 5110 of the second ring 5100. Also, as may be seen in FIG. 5, the second channel 5104 may be defined by a first inner surface 5112 of the first ring 598 and a second inner surface 5114 of the second ring 5100.

In the embodiments shown in FIGS. 5, 5A and 5B, the first ring 598 and the second ring 5100 are parts of a unitary body. However, in alternate embodiments, such as the embodiment of a bleed-over prevention manifold 594' shown in FIG. 5C, the first ring 598' and the second ring 5100' may define separate structures, such as a pair of separate o-rings sandwiched together. Regardless of whether the first ring and the second ring are unitary, however, the function of guiding fluids along their respective paths into the dental syringe tip and preventing bleed-over is the same. Referring to FIG. 5, a first fluid 5114 such as air travels along a first fluid path through a valve, such as a replaceable valve cartridge and enters an outer circumferential channel 5116 defined within the dental syringe tip 510 through one or more orifices 5115 in the dental syringe tip. When the bleed-over prevention manifold 594 comprises a unitary body, this may occur through one or more holes 5117 in the bleed-over prevention manifold. In such an embodiment, the bleed-over prevention manifold may comprise an annular support ring 5119 which strengthens the bleed-over prevention manifold 594 so as to prevent the bleed-over prevention manifold from collapsing under the pressure of the first fluid 5114. As may be seen in FIG. 5A, the annular support ring 5119 may actually be segmented such that fluid may more easily reach the holes 5117 in the bleed-over prevention manifold 594. Further, a second fluid 5118 such as water travels along a second fluid path and enters through an end 5111 of the dental syringe tip 510 and then moves through a centrally defined channel 5120 within the dental syringe tip. In such a configuration, the potential exists for either the first fluid 5114 to bleed-over and enter the inner channel 5120 or the second fluid 5118 to bleed-over and enter the outer channel 5116. The mixing of fluids within a dental syringe tip can be problematic in certain applications making use of a dental syringe such as dental procedures where an adhesive is being used which may fail to adhere properly when exposed to water. For example, water may leak into the outer channel 5116 and come out of the dental syringe when only air is supposed to be dispensed. Accordingly, the bleed-over prevention manifold 594 is designed to prevent bleed-over into the dental syringe tip 510.

Referring to FIG. 5C, the first channel 596' permits any of a first fluid 5114' and a second fluid 5118' which reach the first channel to exit through the bleed path 5102'. This is due to the first channel 596' defining a relatively low pressure zone because the first channel is in fluid communication with the bleed path 5102' which leads to ambient pressure, in comparison to the surrounding areas which are exposed to the pressurized first fluid 5114' and second fluid 5118'. Accordingly, any of either the first fluid 5114' or the second fluid 5118' which passes respective ones of the first ring 598' or the second ring 5100' or otherwise enters the first channel 596' is permitted to exit through the bleed path 5102', rather than mix within the dental syringe tip 510. In embodiments in which there is a second channel 5104, such as the embodiment of FIG. 5B, any such leaking first fluid 5114 or second fluid 5118 may travel from the second channel through one or more holes 5106 to the first channel 596 before exiting the bleed-over prevention manifold 594, as described above. Any such leakage may occur due to leakage past the rings, as described above. Or, the leakage may occur due to a tear in a seal, as, for example, resulting from a seal being cut by syringe tip that has had its end damaged, or which has a burr of metal material on it.

Referring now to FIG. 6, a dental syringe may comprise a system to remove a residual liquid from a tip of a dental syringe, such as included in a replaceable valve cartridge. This system may be useful after a dental syringe dispenses water, and thereafter a drop of water remains on the tip of the dental syringe. As described above, the mixing of fluids within a dental syringe tip can be problematic in certain applications making use of a dental syringe such as procedures where an adhesive is being used which may fail to adhere properly when exposed to water. Thus, an embodiment of a system and an apparatus to remove a residual liquid from a tip of a dental syringe will first be described, followed by embodiments of corresponding methods. FIGS. 6A-6C illustrate an embodiment of a system 6122 to remove residual liquid from a tip of a dental syringe having supplies of a liquid and the second fluid thereto. In the illustrated embodiment, a body 656 defines a cavity 662''' comprising an inlet 6126, an outlet 6128, an outlet sealing surface 6130. The body 656 may comprise the housing of the previously described replaceable valve cartridge when the system 6122 is part of a replaceable valve cartridge. A movable stopper 6132 may be located within the cavity 662''' and may be configured to be sealable against the outlet sealing surface 6130. Further, a plunger 6134 may be configured to be able to move in a first direction along a longitudinal axis of the plunger against the force of a spring 6136 to at least partially enter the cavity 662''', such as through the outlet 6128 and contact the moveable stopper 6132. The plunger 6134 may be further configured to be able to move in a second direction under the force of the spring 6136, substantially opposite to the first direction such that a flow path is formed through the inlet 6126, the cavity 662''', the outlet 6128, and an outlet channel 6137 in fluid communication with the tip of a dental syringe.

FIGS. 6A-6C illustrate the operation of the system 6122 to remove residual fluid, typically a liquid such as water, from a tip of a dental syringe. FIG. 6A illustrates an embodiment of the system 6122 in which a pressurized second fluid 6114, typically a gas such as air, is supplied to the dental syringe but no water is presently being dispensed from the dental syringe. As illustrated within this embodiment, the cavity 662''' enclosing a movable stopper 6132 may be in fluid communication with a second cavity 662' connected to the pressurized air 6114. Such fluid communication may occur through a channel 6138. Further, the second cavity 662' may comprise a flow regulating valve 612 controlling the flow of the air 6114. Thus, as shown, the pressurized supply of air 6114 forces the movable stopper 6132 against the outlet sealing surface 6130 so as to at least partially seal the outlet 6128.

As shown in FIG. 6B, as the plunger 6134 is displaced in a first direction along the longitudinal axis of the plunger such as by actuation of a lever 640, which may also operate a valve controlling dispensing of the water to the tip of a dental syringe, the plunger displaces the moveable stopper 6132 from the outlet sealing surface 6130. Depending upon the orientation of the cavity 662''' with respect to a vertical direction, the movable stopper 6132 may travel in the first direction to the opposite end of the cavity under the force of gravity where the moveable stopper may come to rest on the inlet surface 6140.

Referring now to FIG. 6C, when the plunger 6134 returns in a second direction substantially opposite to the first direction as the lever 640 is released and hence the water supply to the tip of the dental syringe ceases, the pressure from the air 6114 forces the plunger to move beyond its original resting position to a position which is displaced in the second direction. In such a position, the plunger 6134 separates from surrounding structure to create an opening 6142 which is in fluid communication with the dental syringe tip through the outlet channel 6137. Thus, a puff of the air 6114 may travel through the inlet 6126, into the cavity 662″, around the movable stopper 6132, out the outlet 6128 and opening 6142, and through the outlet channel 6137 to the dental syringe tip to remove residual water at the end of the dental syringe tip. The air 6114 is able to pass the movable stopper 6132 because the moveable stopper has dimensions relatively smaller than that of the cavity 662‴. In particular, in some embodiments, the cavity 662‴ may be substantially cylindrical and define a cavity radius. In such embodiments, the moveable stopper 6132 may define a stopper radius wherein the stopper radius is smaller than the cavity radius, but large enough so that the air 6114 pressure creates a seal.

The relative dimensions between the movable stopper 6132 and the cavity 662‴ may at least partially determine the length of time during which the air 6114 flows out of the outlet 6130 and opening 6142 before the movable stopper is returned to the first position as shown in FIG. 6A at which the moveable stopper rests against the outlet sealing surface 6130. In particular, a tighter fit between the moveable stopper 6132 and the cavity 662‴ may cause the moveable stopper to move rapidly under the force of the pressurized air 6114 as there would be less room for the air 6114 to move past the moveable stopper than if not a tight fit. A tight fit refers to one in which the radius of the moveable stopper 6132 is close to that of the cavity 662‴. Once the movable stopper 6132 returns to the outlet sealing surface 6130, the plunger 6134 also returns to an unbiased position as shown in FIG. 6A. As described above, in certain embodiments, the plunger 6134 may be configured to be actuated by a lever 640 that also actuates a water supply to the tip of the dental syringe. Thus, a puff of the air 6114 may automatically occur after each time the valve in fluid communication with the water supply dispenses a flow of water. Accordingly, as described above, this may remove any residual water from the tip of a dental syringe, which may be beneficial during certain dental procedures.

The system 6122 to remove residual water from the tip of a dental syringe may further comprise an outlet spring 6133 which is configured to bias the moveable stopper 6132 away from the outlet sealing surface 6130. For example, the outlet spring 6133 could comprise a coil spring which extends from the outlet sealing surface 6130 toward the moveable stopper 6132. The outlet spring 6133 may assist in the operation of the system 6122 when operating in positions where the system is tilted beyond horizontal by applying a small force on the moveable stopper 6132 which is strong enough to bias the moveable stopper away from the outlet sealing surface 6130, but which is not strong enough to bias the moveable stopper away from the outlet sealing surface when the air 6114 applies pressure to the moveable stopper. Accordingly, as described above, the outlet spring 6133 may enable a puff of air 6114 to travel past the moveable stopper 6132 even when the system is oriented such that gravity pulls the moveable stopper in the second direction toward the outlet sealing surface 6130 because the outlet 6128 may remain at least partially open due to the outlet spring biasing the moveable stopper away from the outlet sealing surface.

FIG. 6D illustrates an additional embodiment of a system 6122a to remove residual water from the tip of a dental syringe. This system 6122a is substantially similar to the above-described system 6122 illustrated in FIGS. 6A-C with small differences as will be described. The system 6122a may comprise a plunger 6134a which is configured to displace a moveable stopper 6132a from an outlet sealing surface 6130a. A pressurized supply of air 6114a forces the movable stopper 6132a against an outlet sealing surface 6130a so as to at least partially seal the outlet 6128a. When the plunger 6134a is depressed, it contacts the moveable stopper 6132a and thereby displaces the moveable stopper 6132a from the outlet sealing surface 6130a and equalizes pressure on the stopper in all directions, as in the previously described embodiment. At the same time, water travels through the system 6122a from an inlet 6980a to an outlet 6982a and to a syringe tip as previously described. However, when the plunger 6134a is released, an opening 6142a allows the pressurized supply of air 6114a to flow through the cavity 662a′ in which the moveable stopper 6132a is located to an outlet channel 6137a to thereby remove any residual water from the tip of the dental syringe. In some embodiments the opening 6142a may comprise one or more holes through the plunger 6134a which do not allow for fluid communication between the cavity 662a‴ and the outlet channel 6137a when the plunger is depressed (due to the opening being entirely below a seal 6184a), but which do allow for fluid communication after the plunger is released (due to the opening defining a flow path past the seal) until the moveable stopper 6132a returns to the outlet sealing surface 6130a. Accordingly, embodiments of a different system 6122a for removing liquid from the tip of a dental syringe are also provided.

Although the above-described system may remove residual water from a tip of a dental syringe, other systems and apparatuses may be used for the same function. Accordingly, as shown in FIG. 7A, a method of removing a residual liquid from a tip of a dental syringe having supplies of a liquid and a second fluid thereto, is provided. The method may comprise actuating a single actuator as shown above at block 7144 to dispense a liquid from a tip of the dental syringe as shown at block 7146. Actuating the single actuator may further automatically dispense the second fluid out of the tip of the dental syringe following the dispensing of the liquid as shown at block 7148. Accordingly, the second fluid substantially removes the residual liquid from the tip of the dental syringe as shown at block 7150. In certain embodiments the liquid may comprise water as shown at block 7152 and the second fluid may comprise air as shown at block 7154. As previously described, water and air are often used in dental syringes. Further, as also previously described, accidental application of water during certain dental procedures can be detrimental and therefore use of air to remove residual water can be beneficial.

Automatically dispensing the second fluid out of the tip of the dental syringe following the dispensing of the liquid may further comprise dispensing a controlled quantity of the fluid 7156. Additionally, the step of automatically dispensing the second fluid out of the tip of the dental syringe following the dispensing of the liquid may further comprise dispensing the second fluid for a controlled period of time 7158. Accordingly, a desired quantity of the second fluid may be dispensed, or a desired duration of dispensing of the second fluid may be obtained. For example, with regard to the system 6122 discussed in FIGS. 6A-6C, the relative dimensions of the movable stopper 6132 and the cavity 662''' may have an effect on both of these factors, with closer relative dimensions resulting in shorter durations and smaller quantities of the second fluid. Therefore, controlled quantities and durations of dispensing of the second fluid may be obtained, for example, by empirical testing using different dimensions for the moveable stopper 6132 and the cavity 662'''.

An additional method and system for removing residual water from a tip of a dental syringe having supplies of water and air thereto is provided in FIG. 7B. The system may comprise a controller 7176 in communication with a water sensor 7178 and an air sensor 7184. The water sensor 7178 may be in communication with a water valve 7180, which controls the dispensing of water from a water source 7182. Similarly, the air sensor 7184 may be in communication with an air valve 7186, which controls the dispensing of air from an air source 7188.

The method associated with the above described system may operate as follows. The method may involve starting, as shown at block 7160, followed by waiting for the water to flow, as shown at block 7162. The method may further comprise checking whether the water is flowing, as shown at block 7164. If the water is not flowing, the method may return to waiting for the water to flow, as shown at block 7162. If the water is flowing, the method may further comprise waiting for the water to stop flowing, as shown at block 7166, and checking whether the water has stopped flowing, as shown at block 7168. If the water has not stopped flowing, the method may return to waiting for the water to stop flowing, as shown at block 7166. If the water has stopped flowing, the method may further include flowing air, as shown at block 7170. Whether or not the water is flowing or has stopped flowing may be determined, for example, using the water sensor 7178.

The above flow of air may remove residual water from a tip of a dental syringe, as described previously. Additionally, the method may further comprise determining whether the water has flowed for a desired duration, as shown at block 7172, or additionally or alternatively, determining whether the desired quantity of air has flowed, as shown at block 7174. The signal from the air sensor 7184 may be used to make these determinations. The entire method may return to the start, as shown at block 7180, if either or both of the desired duration or quantity of air flow has been achieved. While the above description of a method has referenced particular system components, one of ordinary skill in the art would understand that various other electrical and or mechanical components may be used. Further, while the above system and method are described in terms of water and air, one of ordinary skill in the art would understand that various other fluids could be used.

Although embodiments of the invention are generally described in terms of use with a dental syringe, it should be appreciated that various embodiments may be useable in applications outside of the dental syringe context. For example, the flow regulating valves may be useable in many applications where flow-regulating valves, such as needle valves and ball valves, are currently used, such as with nozzles for garden hoses. Accordingly, embodiments of the invention should be considered to be applicable to many different applications and useable in many different industries.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A valve, comprising:
   a body;
   a flow passageway defined within the body;
   a flow-control seal positioned within the flow passageway;
   a piston extending through the flow passageway and the flow-control seal, the piston defining a first direction and a second direction of an axis;
   a flow-control groove defined in the piston, wherein the flow-control groove defines a depth extending into the piston, and wherein the flow-control groove does not extend around the entire circumference of the piston;
   a fluid supply conduit in fluid communication with a first portion of the flow passageway extending from the flow-control in the second direction, the fluid supply conduit configured to provide a fluid flow applied at the perimeter of the piston in the first portion of the flow passageway;
   a fluid outlet conduit in fluid communication with a second portion of the flow passageway;
   a force means configured to apply a force on the piston in the first direction along the axis;
   wherein the flow-control seal contacts the body and the piston and thereby separates the first portion and the second portion of the flow passageway to substantially prevent fluid communication between the first portion and the second portion of the flow passageway when the piston is in a first position wherein the flow-control groove is displaced from the flow-control seal in the first direction;
   wherein, when the piston is displaced in the second direction, opposite to the first direction to a second position, the flow-control groove extends at least partially beyond the flow-control seal in both the first direction and the second direction, whereby the fluid supply conduit is in fluid communication with the fluid outlet conduit through the first portion and the second portion of the flow passageway;
   wherein the depth of the flow-control groove gradually increases in the first direction from a proximal end to a distal end to be configured to gradually increase the flow of fluid between the first portion and the second portion of the flow passageway as the piston is displaced in the second direction.

2. The valve of claim 1, further comprising a first centering sleeve positioned within the flow passageway, wherein the piston extends through the first centering sleeve to thereby substantially prevent movement of the piston other than in the first direction and the second direction along the axis.

3. The valve of claim 2 further comprising a first retaining member, the first retaining member extending at least partially through the body and at least indirectly contacting the first centering sleeve to thereby restrain movement of the first centering sleeve and the flow-control seal at least in the first direction.

4. The valve of claim 3 further comprising a second retaining member, the second retaining member coupling to the piston in a cavity, whereby movement of the piston in the first direction is at least partially restrained by indirect contact between the second retaining member and the first retaining member through at least the centering sleeve and the flow-control seal.

5. The valve of claim 2 wherein the first centering sleeve is positioned in the first portion of the flow passageway, and wherein the first centering sleeve comprises an inlet aperture through which fluid communication between the fluid supply conduit and the flow-control groove occurs when the piston is displaced in the second direction.

6. The valve of claim 5 further comprising a second centering sleeve positioned within the second portion of the flow passageway, wherein the second centering sleeve comprises an outlet aperture through which fluid communication between the flow-control groove and the fluid outlet conduit occurs when the piston is displaced in the second direction.

7. The valve of claim 1, wherein the force means comprises a spring configured to apply a spring force on the piston in the first direction along the axis.

8. The valve of claim 7 wherein the spring is positioned within a cavity in communication with a cavity pressure, wherein the cavity pressure is less than the pressure in the fluid supply conduit.

9. The valve of claim 8, wherein the cavity pressure is ambient air pressure.

10. The valve of claim 9 wherein the cavity is in communication with ambient air pressure through a pressure relief conduit.

11. The valve of claim 1, wherein the fluid supply conduit comprises a metering screw, the metering screw comprising a cylindrical end portion which is configured to be received by a metering cavity in the body, the metering cavity comprising a cylindrical end cavity,
  wherein the cylindrical end portion is moveable from an extended position to a retracted position,
  wherein when the cylindrical end portion is in the extended position, the metering screw occupies a first occupied volume of the metering cavity,
  wherein when the cylindrical end portion is in the retracted position, the metering screw occupies a second occupied volume of the metering cavity, and
  wherein the second occupied volume is less than the first occupied volume.

12. The valve of claim 11, wherein the fluid supply conduit is in fluid communication with the first portion of the flow passageway when the cylindrical end portion is in the extended position and the retracted position.

13. The valve of claim 11, wherein the cylindrical end portion comprises a compressible end portion, wherein the compressible end portion is configured to compress against the body and radially expand when the cylindrical end portion is in the extended position to substantially prevent flow of a fluid through the metering cavity.

14. The valve of claim 1, wherein the flow-control groove is configured to permit increasing flow of fluid through the valve as the piston is displaced in the second direction.

15. The valve of claim 1, wherein the force means comprises a fluid source configured to supply a fluid force to the piston.

16. The valve of claim 1, wherein the total area of the piston perpendicular to the axis which is exposed to force from the fluid in the second direction is greater than the total area of the piston perpendicular to the axis which is exposed to force from the fluid in the first direction.

17. The valve of claim 1, wherein the total area of the piston perpendicular to the axis which is exposed to force from the fluid in the second direction is equal to the total area of the piston perpendicular to the axis which is exposed to force from the fluid in the first direction.

18. The valve of claim 1, wherein the total area of the piston perpendicular to the axis which is exposed to force from the fluid in the second direction is less than the total area of the piston perpendicular to the axis which is exposed to force from the fluid in the first direction.

19. The valve of claim 1 further comprising a flow passageway end seal configured to substantially prevent fluid from escaping out of the flow passageway in the first direction.

20. A method of controlling a flow of fluid, comprising:
  providing a valve comprising a piston defining a flow-control groove and extending through a flow passageway defined in a body along a first direction and a second direction of an axis and a flow-control seal positioned within the flow passageway, wherein the flow-control groove defines a depth extending into the piston, wherein the flow-control groove does not extend around the entire circumference of the piston, wherein the flow-control seal separates the flow passageway into a first portion, extending from the flow-control seal in the second direction, and having a fluid flow supplied thereto, and a second portion;
  providing a force means configured to apply a force to the piston in the first direction along the axis defined by the piston;
  displacing the piston in the second direction along the axis opposite to the first direction to bring the first portion and the second portion of the flow passageway into fluid communication through the flow-control groove and thereby allow the fluid to flow through the valve, wherein the depth of the flow-control groove gradually increases in the first direction from a proximal end to a distal end so as to gradually increase the flow of fluid between the first portion and the second portion of the flow passageway as the piston is displaced in the second direction;
  releasing the piston, whereby the force means displaces the piston including the flow-control groove in the first direction and thereby prevents fluid communication between the first portion and the second portion of the flow passageway and prevents flow of the fluid through the valve.

21. The method of claim 20, wherein the valve further comprises a first centering sleeve positioned within the flow passageway, wherein the piston extends through the first centering sleeve to thereby substantially prevent movement of the piston other than in the first direction and the second direction along the axis, wherein the first centering sleeve is positioned in the first portion of the flow passageway, and wherein the first centering sleeve comprises an inlet aperture through which fluid communication between the fluid supply conduit and the flow-control groove occurs when the piston is displaced in the second direction.

22. A valve, comprising:
  a body;
  a flow passageway defined within the body;
  a flow-control seal positioned within the flow passageway;
  a piston extending through the flow passageway and the flow-control seal, the piston defining a first direction and a second direction of an axis;
  a flow-control groove defined in the piston, wherein the flow-control groove defines a depth extending into the piston, and wherein the flow-control groove does not extend around the entire circumference of the piston;
  a fluid supply conduit in fluid communication with a first portion of the flow passageway extending from the flow-control in the second direction, the fluid supply conduit configured to provide a fluid flow applied at the perimeter of the piston in the first portion of the flow passageway;

a fluid outlet conduit in fluid communication with a second portion of the flow passageway;

a force means configured to apply a force on the piston in the first direction along the axis; and a first centering sleeve positioned within the flow passageway, wherein the piston extends through the first centering sleeve to thereby substantially prevent movement of the piston other than in the first direction and the second direction along the axis, wherein the first centering sleeve is positioned in the first portion of the flow passageway, and wherein the first centering sleeve comprises an inlet aperture through which fluid communication between the fluid supply conduit and the flow-control groove occurs when the piston is displaced in the second direction;

wherein the flow-control seal contacts the body and the piston and thereby separates the first portion and the second portion of the flow passageway to substantially prevent fluid communication between the first portion and the second portion of the flow passageway when the piston is in a first position wherein the flow-control groove is displaced from the flow-control seal in the first direction;

wherein, when the piston is displaced in the second direction, opposite to the first direction to a second position, the flow-control groove extends at least partially beyond the flow-control seal in both the first direction and the second direction, whereby the fluid supply conduit is in fluid communication with the fluid outlet conduit through the first portion and the second portion of the flow passageway.

23. The valve of claim 22 further comprising a second centering sleeve positioned within the second portion of the flow passageway, wherein the second centering sleeve comprises an outlet aperture through which fluid communication between the flow-control groove and the fluid outlet conduit occurs when the piston is displaced in the second direction.

* * * * *